United States Patent
Yang et al.

(10) Patent No.: US 12,234,257 B2
(45) Date of Patent: Feb. 25, 2025

(54) TRITERPENE SAPONIN DERIVATIVE AND USE THEREOF

(71) Applicant: KOREA INSTITUTE OF SCIENCE AND TECHNOLOGY, Seoul (KR)

(72) Inventors: Hyun Ok Yang, Gangneung-si (KR); Hak Cheol Kwon, Gangneung-si (KR); Li Jun Zhang, Gangneung-si (KR); Jaeyoung Kwon, Gangneung-si (KR); Kee Beom Ko, Gangneung-si (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 513 days.

(21) Appl. No.: 17/199,651

(22) Filed: Mar. 12, 2021

(65) Prior Publication Data

US 2021/0284677 A1    Sep. 16, 2021

(30) Foreign Application Priority Data

Mar. 12, 2020 (KR) .................. 10-2020-0030814

(51) Int. Cl.
| | |
|---|---|
| *C07H 15/24* | (2006.01) |
| *A23L 33/00* | (2016.01) |
| *A23L 33/105* | (2016.01) |
| *A61K 9/00* | (2006.01) |
| *A61P 25/28* | (2006.01) |

(52) U.S. Cl.
CPC ............ *C07H 15/24* (2013.01); *A23L 33/105* (2016.08); *A23L 33/30* (2016.08); *A61K 9/0053* (2013.01); *A61P 25/28* (2018.01)

(58) Field of Classification Search
CPC ........ A23L 33/105; A23L 33/30; C07H 15/24
See application file for complete search history.

(56) References Cited

PUBLICATIONS

Lee et al., International Journal of Molecular Sciences, 2023, 24, 5765, 1-23 (Year: 2023).*
Intelihealth 2007, http://www.intelihealth.com/IH/ihtIH/WSIHW000/8303/9117/195703.html?d=dmtHealthAZ (Year: 2007).*
Mayoclinic, 2024, https://www.mayoclinic.org/diseases-conditions/parkinsons-disease/symptoms-causes/syc-20376055#:~:text=Because%20the%20cause%20of%20Parkinson'sthe%20risk%20of%20Parkinson's%20disease (Year: 2024).*
Victor H. Castro et al., "Structures and Antiproliferative Activity of Saponins from Sechium pittieri and S. talamancense," Chem. Pharm. Bull., 1997, pp. 349-358, vol. 45, No. 2.
Tsuneatsu Nagao et al., "Studies on the Constituents of Luffa acutangula ROXB. II. Structures of Acutosides H and I, Oleanolic Acid Saponins Isolated from the Seed," Chem. Pharm. Bull., 1991, pp. 889-893, vol. 39, No. 4.
Beatriz Hernandez-Carlos et al., "Bioactive saponins from Microsechium helleri and Sicyos bulbosus," Phytochemistry, 2011, pp. 743-751, vol. 72, Elsevier Ltd.

(Continued)

*Primary Examiner* — San Ming R Hui
(74) *Attorney, Agent, or Firm* — CANTOR COLBURN LLP

(57) ABSTRACT

Provided are astersaponin I, which is a novel triterpene saponin derivative isolated and identified from a *Aster koraiensis* Nakai (Korean starwort) extract, and a use thereof for preventing or treating a neurodegenerative disorder.

6 Claims, 25 Drawing Sheets

(56) References Cited

PUBLICATIONS

Asma Alaoui et al., "Triterpenoid Saponins from the Shells of Argania spinosa Seeds," J. Agric. Food Chem., 2002, pp. 4600-4603, vol. 50, American Chemical Society.

Piotr Ruszkowski et al., "Natural Triterpenoids and their Derivatives with Pharmacological Activity Against Neurodegenerative Disorders," Mini-Reviews in Organic Chemistry, 2014, pp. 307-315, vol. 11, Bentham Science Publishers.

Korean Notice of Allowance for KR Application No. 10-2020-0030814 mailed on Nov. 17, 2021, citing the above reference(s).

Cesario V. Borlongan, et al., Striatal Dopamine-Mediated Motor Behavior Is Altered Following Occlusion of the Middle Cerebral Artery, Pharmacology Biochemistry and Behavior, vol. 52, No. 1, pp. 225-229, 1995.

Dong-Young Choi, et al., Lack of CCR5 modifies glial phenotypes and population of the nigral dopaminergic neurons, but not MPTP-induced dopaminergic neurodegeneration, Neurobiology of Disease 49 (2013) 159-168.

Noboru Mizushima, Methods for monitoring autophagy, The International Journal of Biochemistry & Cell Biology 36 (2004) 2491-2502.

Wei Zhu, et al., Changes in motor function, cognition, and emotion-related behavior after right hemispheric Intracerebral hemorrhage in various brain regions of mouse, Brain, Behavior, and Immunity 69 (2018) 568-581.

Xiang-Dong Su, et al., Anti-inflammatory Potential of Saponins from Aster tataricus via $NF_{K}B$/MAPK Activation, American Chemical Society and American Society of Pharmacognosy, Received: Oct. 15, 2018, 10 pp.

XiaoLong Hu, et al., Neuroprotective effects of Kukoamine A on neurotoxin-induced Parkinson's model through apoptosis inhibition and autophagy enhancement, Neuropharmacology 117 (2017) 352-363.

\* cited by examiner

TRITERPENE SAPONIN DERIVATIVE AND USE THEREOF

TECHNICAL FIELD

The present invention relates to astersaponin I, which is a novel triterpene saponin derivative isolated and identified from an extract of *Aster koraiensis* Nakai (Korean starwort), and a use thereof for preventing or treating a neurodegenerative disorder.

BACKGROUND ART

As the phenomenon of an aging society with a gradual increase in the population of elderly people has recently become a societal issue, neurodegenerative disorders have increasingly gained attention. Neurodegenerative disorders are diseases characterized by disability in motor function, memory, cognitive function, or the like caused by degeneration of nerves due to various causes. Among them, Parkinson's disease is a representative neurodegenerative disorder with the second highest incidence after Alzheimer's disease. Parkinson's disease is named after the English doctor James Parkinson, who published the first detailed description in an essay on "shaking palsy" in 1817, the term Parkinson's disease was first used by J. Charout 60 years thereafter, and it was confirmed that Parkinson's disease is related to the extrapyramidal system and not the pyramidal system in the central pathways of the spinal cord by Kinner Wilson in 1912.

Although studies for determining causes of the Parkinson's disease have been conducted over several decades, the mechanism has not been accurately revealed. Thus, Parkinson's disease is classified as an incurable disease with progressive neurological disorder without effective and efficient long-term therapeutic methods therefor. However, it is assumed that Parkinson's disease is caused by various pathological factors occurring in patients with Parkinson's disease. One of the representative factors is abnormal death of nerve cells that secrete dopamine among neurotransmitters distributed in substantia nigra par compacta of the midbrain when the substantia nigra par compacta of the midbrain is destroyed or damaged. Abnormal death of dopaminergic neurons occurs via a series of processes. First, mitochondria damaged by various factors such as environment, heredity, and aging cause dysfunction in the protein degradation system, resulting in accumulation of abnormal proteins and organelles that have not been degraded. Due to such causes, the importance of the protein degradation system has been highlighted in treatment and prevention of Parkinson's disease.

In clinical settings, L-DOPA has been the most commonly prescribed medication to date for patients with Parkinson's disease, and increases the concentration of dopamine in the blood by directly injecting Levodopa, which is a precursor of dopaminergic neurons. Although direct injection of Levodopa substantially alleviates the symptoms of patients with Parkinson's disease, long-term use thereof inevitably increases dose escalation, which is known to cause various unexpected side-effects. Therefore, instead of therapeutic methods of directly administering L-DOPA, which increases the concentration of dopamine in the blood, there is an urgent need to develop more fundamental medical treatment and drugs capable of protecting nerve cells secreting dopamine and preventing death thereof. As one of these attempts, research into development of a therapeutic agent targeting autophagy, one of the protein degradation systems, has received attention in recent years.

Autophagy is a word derived from the Greek words for "self" and "eating", and has been known as a mechanism of sacrifice to maintain the metabolic balance of cells and which has an important role in the fate of cells. Autophagy has a morphological structure characterized in that the edges of a phagophore, which is a precursor of an autophagosome having the form of independent double membranes, gradually extend to engulf an unnecessary protein in a cell to form an autophagosome, which is an endoplasmic reticulum. In addition, it has been reported that the autophagosome migrates along microtubules to fuse with a lysosome in the cell to form an autolysosome, and a protease secreted by the lysosome degrades the protein. Autophagy not only regulates the balance of energy sources and adaption of nutrient stress, but also promotes the degradation of damaged cytosolic components or organelles before they become toxic to cells. Autophagy is very important for the treatment of various diseases including neurodegenerative disorders. A decline of autophagy results in the accumulation of toxic components in cytoplasma and ultimately leads to neurodegenerative disorders such as Parkinson's disease (PD). During the autophagy process, microtubule-associated protein light chain 3 (LC3) is conjugated with phosphatidylethanolamine to form LC3-II, which is found on the membranes of autophagosomes. Since the formation of LC3-II reflects the amount of autophagosomes, LC3 has been regarded as an important marker to monitor autophagy induction.

Meanwhile, *Aster koraiensis* Nakai (Korean starwort), belonging to the family Asteraceae, is a perennial herb originating in Korea and mainly distributed in temperate regions of the Korean peninsula and Jeju island. This plant has long been utilized for decoration, food ingredients, and traditional medicines. Its young leaves and stems are edible, and the roots have been used for the treatment of chronic bronchitis, pertussis, and pneumonia. Previous phytochemical studies demonstrated that it contains polyacetylene, benzofuran, and sesquiterpenoids, which are associated with several biological activities, such as cytotoxicity and immune diseases. Also, various uses of *Aster koraiensis* extracts have been known, for example, effects on treating wounds or inducing skin regeneration, skin whitening effects, anti-diabetic activity, alleviating effects on dry eye syndrome, collagen-related skin anti-aging effects, alleviating effects on retinal diseases, protective effects on liver, alleviating effects on obesity and hyperlipidemia, pain treatment effects, anti-cancer effects, and alleviating effects on diabetic complications have been reported. Although the present inventors have confirmed in prior research that extracts of *Aster koraiensis* have preventive or therapeutic effects on neurodegenerative disorders such as Parkinson's disease, no specific active ingredients exhibiting the above effects have been confirmed.

Astersaponin is mainly isolated and reported from *Aster tataricus* L. and has structural characteristics in which hydroxyl groups and a sugar moiety such as arabinopyranose, glucopyranose, apiofuranose, xylopyranose, or rhamnopyranose bound to C-3 and C-2 or C-16 of an oleanane triterpene parent structure are substituted at the hydroxyl group of C-3 and a carboxylic acid located at C-28. To date, 11 types of astersaponin (astersaponin A, $A_2$, B, C, $C_2$, E, F, G, $G_2$, H, and $H_b$) have been reported, inhibitory effects on nitrogen oxide (NO) production in cells, cytotoxic effects on cancer cells, and anti-inflammatory action have been reported. Astersaponin may have different physiological activities according the substitution position of the hydroxyl group and the type and position of the bound sugar moiety. For example, superior anti-inflammatory action of astersaponin B compared to other astersaponins has been reported, wherein astersaponin B is characterized by a structure in which a hydroxyl group exists at C-16 and apiofuranose and xylopyranose are located at terminals of a sugar moiety binding to the carboxylic acid at C-28 (Su, Xiang-Dong et al. *Journal of Natural Products,* 2019, 82, 1139-1148). However, effects of astersaponin on autophagy induction and neuroprotective activity have not been reported. In particular, the astersaponin I of the present invention, as a novel compound characterized in that a sugar moiety of the terminal of a disaccharide bound to the C-3 of an aglycone parent structure is xylopyranose, a first sugar moiety among five sugar moieties bound to the carboxyl group at C-28 is arabinopyranose, and sugar moieties at the terminal are xylopyranose and rhamnopyranose, has not been reported to date. In addition, astersaponin I, which includes five sugar moieties, consisting of one arabinopyranose unit, two xylopyranose units, and two rhamnopyranose units, bound to the carboxyl group at C-28, is reported for the first time in the present invention. The substance most similar to astersaponin I is conyzasaponin K isolated and reported from the plant *Conyza blini*. However, although the composition and the order of linkage of the two sugar moieties bound to C-3 of the aglycone precursor are the same, conyzasaponin K has a different structure since one terminal sugar moiety of the five sugar moieties bound to the carboxyl group at C-28 is apiofuranose, whereas this is xylopyranose in astersaponin.

As a result of intensive efforts to isolate a biologically active compound exhibiting autophagy-inducing activity which has an important role in treating neurodegenerative disorders from an extract of *Aster koraiensis*, the present inventors have confirmed that astersaponin I (hereinafter referred to as Compound 1), as a novel triterpene saponin isolated and identified from an ethanol extract of *Aster koraiensis*, induces autophagy by significantly increasing the expression of microtubule-associated protein light chain 3B (LC3-II) in SH-SY5Y cells, thereby completing the present invention.

DISCLOSURE

Technical Problem

An object of the present invention is to provide a compound represented by Formula 1 below or a pharmaceutically acceptable salt thereof.

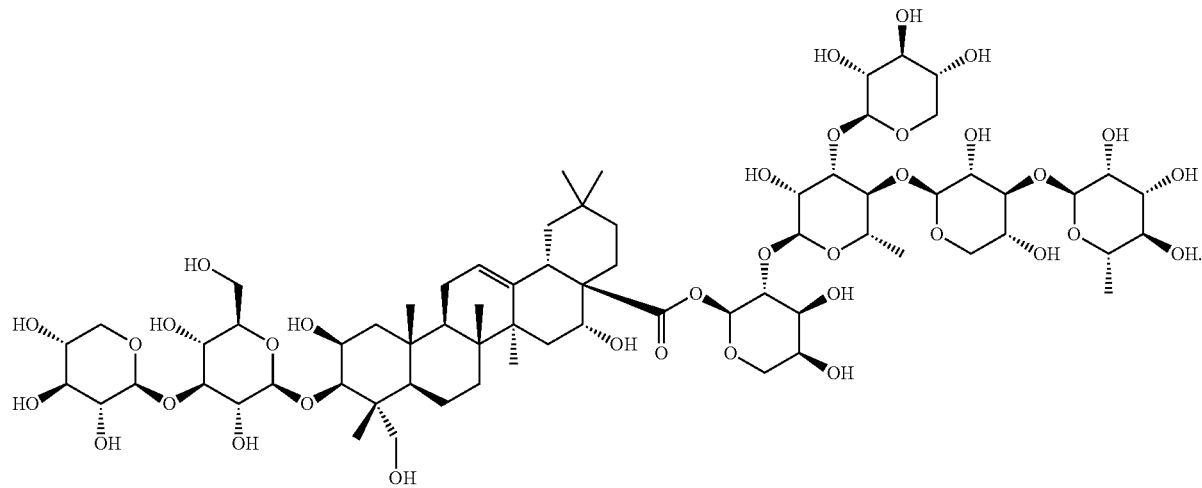

[Formula 1]

Another object of the present invention is to provide a pharmaceutical composition for preventing or treating a neurodegenerative disorder including the compound of Formula 1 or a pharmaceutically acceptable salt thereof as an active ingredient.

Another object of the present invention is to provide a method of preventing or treating a neurodegenerative disorder including administering the pharmaceutical composition to an individual in need thereof.

Another object of the present invention is to provide a food composition for preventing or alleviating a neurodegenerative disorder including the compound of Formula 1 or a sitologically acceptable salt as an active ingredient.

Another object of the present invention is to provide a feed composition for preventing or alleviating a neurodegenerative disorder including the compound of Formula 1 or a sitologically acceptable salt as an active ingredient.

Technical Solution

Each description and embodiment disclosed in the present invention may be applied herein to describe different descriptions and embodiments. In other words, all combinations of various components disclosed in the present invention are included within the scope of the present invention. Furthermore, the scope of the present invention should not be limited by the detailed description provided below.

An aspect of the present invention to achieve the above-described objects provides a compound represented by Formula 1 below or a pharmaceutically acceptable salt thereof.

[Formula 1]

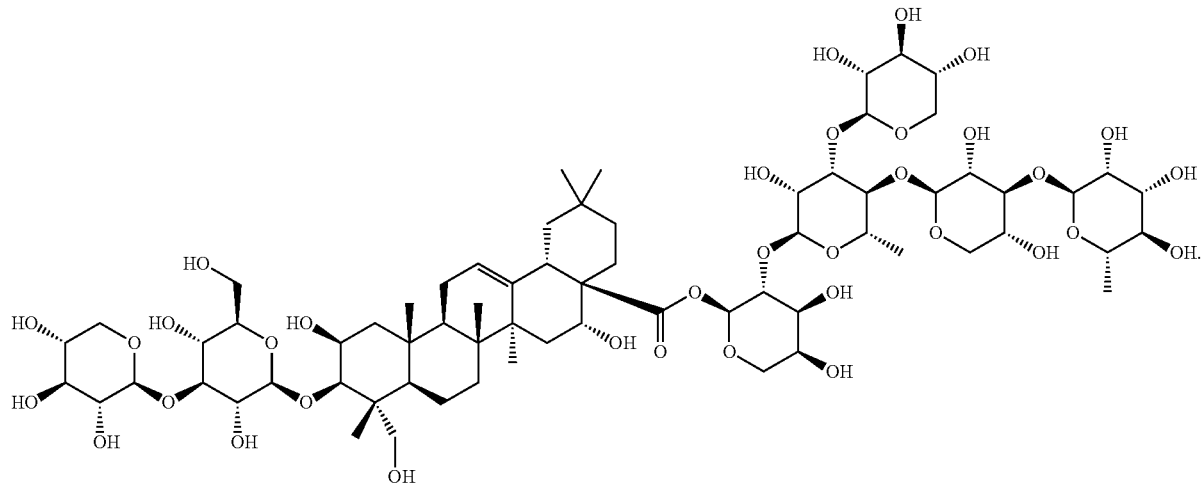

For example, the compound may be a compound isolated from an extract of *Aster koraiensis*. Specifically, the compound may be isolated from an ethanol extract of *Aster koraiensis*, without being limited thereto. Furthermore, the compound may be isolated from a butanol fraction of an extract of *Aster koraiensis*. More specifically, the compound may be isolated from a butanol fraction of an ethanol extract of *Aster koraiensis*, without being limited thereto. The *Aster koraiensis* extract may be obtained from aboveground parts of the plant, e.g., stems and leaves, but is not limited thereto as long as the extract includes the compound. *Aster koraiensis* commercially purchased or harvested in the wild or farmed may be used.

As used herein, the term "extract" encompasses the extract itself and all possible formulations of the extract, such as a liquid extract obtained through extraction of *Aster koraiensis*, a diluent or concentrate of the liquid extract, a dehydrated product obtained by drying the liquid extract, a crude purified product or purified product of the liquid extract, or any mixture thereof.

Methods of preparing the *Aster koraiensis* extract are not particularly limited and may be any method well known in the art. Non-limiting examples of the extraction method may include hot water extraction, ultrasonic extraction, filtration, and reflux extraction, which may be used alone or in a combination of at least two thereof.

In the present invention, types of a solvent used to prepare the *Aster koraiensis* extract are not particularly limited and may be any solvent well known in the art. Non-limiting examples of the solvent may include water, a $C_1$-$C_4$ alcohol, and any mixed solvent thereof, which may be used alone or in a combination of at least two thereof. Specifically, the solvent may preferably be 95% ethanol, without being limited thereto.

As used herein, the term "fraction" refers to a resultant obtained by performing fractionation to isolate a particular component or a particular component group from a mixture of various components.

In the present invention, methods of obtaining the fraction are not particularly limited and may be any method well known in the art. Non-limiting examples of the fractionation method may include solvent fractionation performed by treating with various solvents, ultrafiltration fractionation performed by passing through an ultrafiltration membrane having a specific molecular weight cut-off value, chromatographic fractionation performed by using various chromatographic systems (manufactured for separation based on size, charge, hydrophobicity, or affinity), and any combination thereof. Specifically, any method of obtaining fractions from the extract of *Aster koraiensis* of the present invention by treating the extract with a solvent may be used.

In the present invention, types of a fractionation solvent used to obtain the fraction are not particularly limited and may be any solvent well known in the art. Non-limiting examples of the fractionation solvent may be a polar solvent such as water and a C1-C4 alcohol; or a non-polar solvent such as hexane, ethyl acetate, chloroform, and dichloromethane; or any mixed solvent thereof. These solvents may be used alone or in a combination of at least two thereof but are not limited thereto. Specifically, hexane, ethyl acetate, butanol, or water may be used alone or in a combination of at least two thereof, and more specifically, n-butanol may be used, without being limited thereto.

The compound of the present invention is characterized by autophagy-inducing activity in cells, e.g., brain cells.

Meanwhile, the compound of the present invention may be used in the form of a pharmaceutically acceptable salt. As used herein, the term "pharmaceutically acceptable salt" refers to any salt that possesses desired biological and/or physiological activities of the compound and exhibits minimal unwanted toxicological effects. An acid addition salt formed by a pharmaceutically acceptable free acid may be efficiently used as the salt. The acid addition salt may be prepared by any methods well known in the art, for example, by dissolving the compound in an excess of an aqueous acid solution followed by precipitation of the salt using a water-miscible organic solvent, such as methanol, ethanol, acetone, or acetonitrile. The compound and acid or alcohol in water (e.g., glycol monomethyl ether) in the same molar amount are heated, and then the mixture is dried by evaporation, or precipitated salts may be filtered by suction. In this regard, the free acid may be an inorganic acid or an organic acid. The inorganic acid may be hydrochloric acid, hydrobromic acid, phosphoric acid, nitric acid, sulfuric acid, tartaric acid, or the like, and the organic acid may be methane sulfonic acid, p-toluene sulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, or the like, without being limited thereto.

In addition, a pharmaceutically acceptable metal salt may be prepared by using a base. For example, an alkali metal or alkali earth metal salt is obtained by dissolving the compound in an excess of an alkali metal hydroxide or alkali earth metal hydroxide solution, filtering a non-soluble compound salt, and then evaporating and drying the filtrate. In this regard, as the metal salt, a sodium salt, a potassium salt, or a calcium salt is preferably prepared from a pharmaceutical aspect, without being limited thereto. In addition, a silver salt corresponding thereto may be obtained by reacting an alkali metal or alkali earth metal salt with a suitable silver salt (e.g., silver nitrate).

The pharmaceutically acceptable salt of the compound of Formula 1 may include any salt of an acidic or basic group possibly present in the compound, unless otherwise indicated. For example, the pharmaceutically acceptable salt may include sodium, calcium, and potassium salts of a hydroxyl group, and other pharmaceutically acceptable salts of an amino group may include hydrobromide, sulfate, hydrosulfate, phosphate, hydrophosphate, dihydrophosphate, acetate, succinate, citrate, tartrate, lactate, mandelate, methane sulfonate (mesylate), and p-toluene sulfonate (tosylate), which may be prepared by any method of preparing salts well known in the art.

Another aspect of the present invention provides a pharmaceutical composition for preventing or treating a neurodegenerative disorder including a compound represented by Formula 1 below or a pharmaceutically acceptable salt thereof.

Also, the present invention provides a method of preventing or treating a neurodegenerative disorder, including administering the pharmaceutical composition to an individual in need thereof.

Specifically, prevention or treatment of a neurodegenerative disorder by the compound of Formula 1 of the present invention may be achieved by autophagy-induced neuroprotective action.

As used herein, the term "neurodegenerative disorder" refers to a disease related to symptoms caused when neurons degenerate and lose the function thereof, leading to cell death. Since most neurodegenerative disorders are progressive, results thereof are very destructive, and patients having these diseases may experience extreme degeneration of cognitive or motor capabilities. The neurodegenerative disorders include, but are not limited to, diseases in which autophagy-induced neuroprotective action may effectively work, e.g., Parkinson's disease (PD, Moors, Tim E. et al., *Molecular Neurodegeneration*, 2017, 12:11; Rubinsztein, David C. et al., *Autophagy*, 2005, 1:11), Alzheimer's disease (AD, Nixon, Ralph A., *Journal of Cell Science*, 2007, 120:4081), amyotrophic lateral sclerosis (ALS, Chen, Sheng et al., *Brain Pathology*, 2012, 22:110; Barmada, Sami J et al., *Nature Chemical Biology*, 2014, 10:677), Huntington's disease (HD, Martin, Dale D. O. et al., *Trends in Neurosciences*, 2015, 38:26), Fronto-Temporal Dementia (Winslow, Ashley R. & Rubinsztein, David C., *Biochimica et Biophysica Acta—Molecular Basis of Disease*, 2008, 1782: 723), Corticobasal Degeneration (Piras, Antonio et al., *Acta Neuropathologica Communications*, 2016, 4:22), and progressive supranuclear palsy (PSP, Piras, Antonio et al., *Acta Neuropathologica Communications*, 2016, 4:22). Specifically, a neurodegenerative disorder that may be prevented or treated by administering the pharmaceutical composition of the present invention may be Parkinson's disease, but is not limited thereto.

As used herein, the term "prevention" refers to any action resulting in inhibition or delay of development of a neurodegenerative disorder by administering the compound of

[Formula 1]

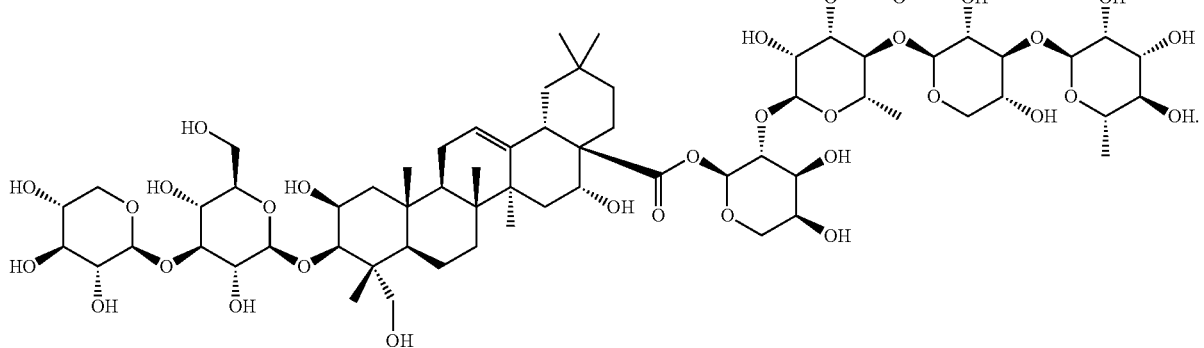

Formula 1, a pharmaceutically acceptable salt thereof, or a pharmaceutical composition including the same as an active ingredient.

As used herein, the term "treatment" refers to any action resulting in improvement or advantageously changed symptoms of a neurodegenerative disorder by administering the compound of Formula 1, a pharmaceutically acceptable salt thereof, or a pharmaceutical composition including the same as an active ingredient.

As used herein, the term "individual" refers to any animal including humans with a neurodegenerative disorder or at risk of developing a neurodegenerative disorder, and the neurodegenerative disorder may be effectively prevented or treated by administering the pharmaceutical composition of the present invention to the individual. The pharmaceutical composition of the present invention may be administered alone or in combination with other existing therapeutic agents for neurodegenerative disorders, sequentially or simultaneously.

As used herein, the term "administering" refers to introducing a particular substance into a patient by any appropriate method. The composition of the present invention may be administered by any general route as long as it is able to reach a target tissue. The composition may be administered via intraperitoneal administration, intravenous administration, intramuscular administration, subcutaneous administration, intradermal administration, oral administration, topical administration, intranasal administration, intrapulmonary administration, or rectal administration, without being limited thereto. Solid formulations for oral administration may include tablets, pills, powders, granules, capsules, and the like, and the solid formulations may be prepared by mixing the composition with at least one excipient, such as starch, calcium carbonate, sucrose, lactose, or gelatin. A lubricant such as magnesium stearate and talc may also be used in addition to a simple excipient. A liquid formulation for oral administration may be a suspension, a formulation for internal use, an emulsion, a syrup, or the like, and may include various excipients such as a humectant, a sweetener, a fragrance, and a preservative in addition to a simple common diluent such as water and liquid paraffin. However, since the active ingredient of *Aster koraiensis* derived from natural substances may be digested upon oral administration, the active ingredient of the composition for oral administration may be coated or formulated for protection against degradation in the stomach. Formulations for parenteral administration may include sterile aqueous solutions, non-aqueous solvents, suspensions, emulsions, lyophilizates, suppositories, and the like. The non-liquid solutions and suspensions may be propylene glycol, polyethylene glycol, vegetable oils such as olive oil, injectable esters such as ethyl oleate, or the like. Bases for the suppositories may include Witepsol, Macrogol, Tween 61, cacao butter, laurin butter, glycerogelatin, and the like.

In addition, the pharmaceutical composition of the present invention may be administered using a certain device capable of delivering the active ingredient into a target cell. Preferred methods or formulations for administration may include intravenous injections, subcutaneous injections, intradermal injections, intramuscular injections, instillation injections, and the like. The injections may be prepared by using an aqueous solvent such as a physiological saline solution and Ringer's solution, or a non-aqueous solvent such as vegetable oil, a higher fatty acid ester (e.g., ethyl oleate), and alcohol (e.g., ethanol, benzyl alcohol, propylene glycol, and glycerin), and may include a pharmaceutical carrier such as a stabilizer to prevent degradation (e.g., ascorbic acid, sodium bisulfite, sodium pyrosulfite, BHA, tocopherol, and EDTA), an emulsifier, a buffer to adjust the pH, and a preservative to inhibit microbial growth (e.g., phenylmercury nitrate, thimerosal, benzalkonium chloride, phenol, cresol, and benzyl alcohol).

The composition may be administered in a pharmaceutically effective amount in a single dosage or multiple dosages. As used herein, the term "pharmaceutically effective amount" refers to an amount sufficient to prevent or treat a disease at a reasonable benefit/risk ratio applicable to any medical prevention or treatment. An effective dosage level may be determined according to factors including severity of illness, activity of a drug, age, body weight, health state, and gender of the patient, sensitivity of the patient to the drug, administration time, administration route, and excretion rate of the composition of the present invention, treatment duration, a drug to be mixed with or concurrently used in combination with the composition of the present invention, and other factors well known in the medical field.

The pharmaceutical composition of the present invention may be administered in an amount of 0.0001 mg/body weight kg to 500 mg/body weight kg, more specifically 0.01 mg/body weight kg to 500 mg/body weight kg per day based on solid content. The pharmaceutical composition may be administered once a day or several times a day in divided doses.

For example, prevention or treatment of the neurodegenerative disorder by the pharmaceutical composition of the present invention may be achieved by inhibiting brain cell death via autophagy-inducing action.

In addition, the pharmaceutical composition of the present invention may further include a pharmaceutically acceptable carrier in addition to the active ingredient. As used herein, the term "pharmaceutically acceptable carrier" refers to a carrier or a diluent used without causing irritation to a living organism and damaging the biological activities and properties of the administered compound. A pharmaceutically acceptable carrier in a composition formulated into a liquid solution may be a carrier sterilized and suitable for a living organism, such as a saline solution, a sterile aqueous solution, Ringer's solution, buffered saline, an albumin injection solution, a dextrose solution, a maltodextrin solution, glycerol, ethanol, and any mixture of at least two thereof, and may further include other additives commonly used in the art such as an antioxidant, a buffer, or a bacteriostatic agent, if necessary.

Another aspect of the present invention provides a food composition for preventing or alleviating a neurodegenerative disorder including the compound of Formula 1 or a sitologically acceptable salt as an active ingredient.

[Formula 1]

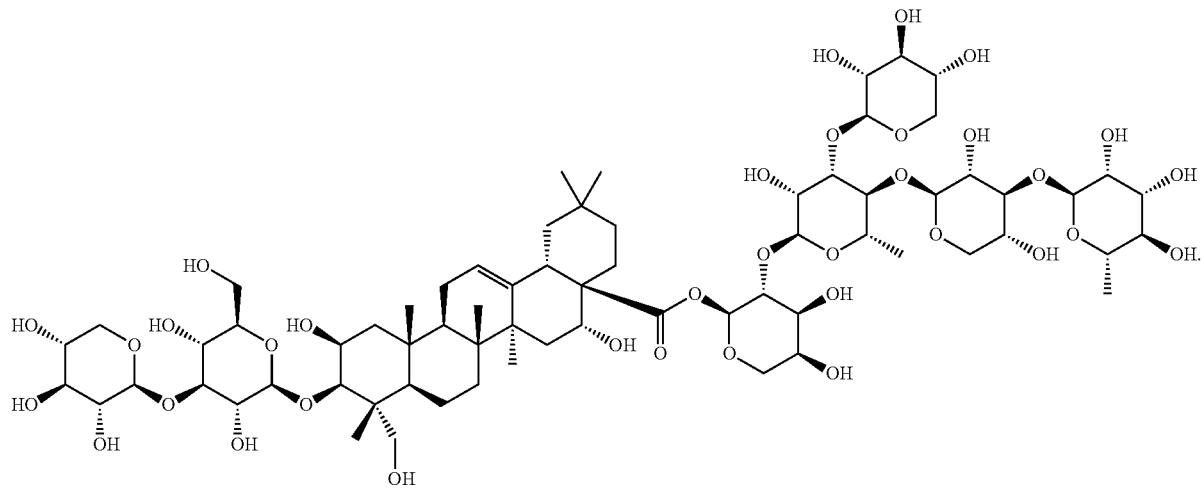

In this regard, the neurodegenerative disorder and prevention are as defined above.

As used herein, the term "sitologically acceptable salt" is as defined above with reference to the "pharmaceutically acceptable salt".

As used herein, the term "alleviation" refers to any action to decrease parameters, e.g., the degree of symptoms, related to a condition to be treated by administering the composition of the present invention.

As used herein, the term "food" includes meats, sausages, breads, chocolates, candies, snacks, cookies, pizzas, ramens, other noodles, gums, dairy products including ice cream, various kinds of soups, beverages, teas, drinks, alcoholic beverages, vitamin complexes, health functional food, and health food, and may also include all foods that are considered within conventional meaning.

Since the food composition of the present invention may be ingested routinely, high effects on alleviating Parkinson's disease may be expected, and therefore, the food composition may be efficiently applied for the purpose of improving health.

Also, the food composition of the present invention may be used as a health functional food. The term "health functional food" refers to food manufactured and processed using raw materials or ingredients beneficial to human health under a law related to health functional food, and the term "functional" refers to regulating nutrients for the structure or function of the human body or providing beneficial effects on health, such as physiological effects. The food composition of the present invention may be prepared by way of a method commonly used in the art, and raw materials and ingredients typically used in the art may be added thereto. In addition, the food composition may be prepared in any formulation acceptable as food, without limitation. The food composition of the present invention may be prepared in various formulations and has advantages over general drugs, such as no side-effects which might occur upon long-term intake of a drug because the food composition is manufactured using natural substances and high portability, and therefore the food composition may be ingested as an aid for promoting alleviative effects on Parkinson's disease.

The health food refers to a food having an effect on actively maintaining or improving a health condition compared to general foods, and the health supplement food refers to a food for health supplement. In some cases, these terms "health functional food", "health food", and "health supplement food" are used interchangeably.

Specifically, the health functional food is a food prepared by adding the extract of the present invention to a food material such as beverages, teas, flavors, gums, confectionery, or the like, or prepared as a capsule, powder, or suspension, and the health functional food means a food that elicits a particular effect on health when consumed. Unlike general drugs, the food composition includes a food as a raw material, and therefore, it has advantages of being free from side-effects that may occur upon long-term intake of a drug.

The food composition may further include a physiologically acceptable carrier, types of the carrier are not particularly limited, and any carrier commonly used in the art may also be used.

Also, the food composition may further include an additional ingredient capable of improving smell, taste, appearance, and the like commonly used in food compositions. For example, the food composition may include vitamins A, C, D, E, $B_1$, $B_2$, $B_6$, and $B_{12}$, niacin, biotin, folate, pantothenic acid, and the like. In addition, the food composition may include minerals such as zinc (Zn), iron (Fe), calcium (Ca), chromium (Cr), magnesium (Mg), manganese (Mn), copper (Cu), and chromium (Cr); and amino acids such as lysine, tryptophan, cysteine, and valine.

Also, the food composition may include food additives such as a preservative (e.g., potassium sorbate, sodium benzoate, salicylic acid, or sodium dehydroacetate), a disinfectant (e.g., bleaching powder, higher bleaching powder, or sodium hypochlorite), an antioxidant (e.g., butylhydroxyanisole (BHA) and butylhydroxytoluene (BHT)), a coloring agent (tar color), a color-developing agent (e.g., sodium nitrate and sodium nitrite), a bleaching agent (e.g., sodium sulfite), a seasoning (e.g., monosodium glutamate (MSG)), a sweetener (e.g., dulcin, cyclemate, saccharin, and sodium), a flavor (e.g., vanillin and lactones), a swelling agent (e.g., alum and potassium D-bitartrate), a fortifier, an emulsifier, a thickener (e.g., adhesive pastes), a film-forming agent, a gum base agent, an antifoaming agent, a solvent, an improver, and the like. The additives may be selected according to the type of food and used in an appropriate amount.

The food composition of the present invention may further include a common food additive, and acceptability thereof as a "food additive" should be determined based on the standards and criteria regarding the corresponding items according to the General Provisions and General Test Methods of the Korean Food Additives Codex approved by the Ministry of Food and Drug Safety, unless specified otherwise.

Items listed in the "Korean Food Additive Codex" may be, for example, chemical compounds such as ketones, glycine, potassium citrate, nicotinic acid, and cinnamic acid, natural additives such as persimmon color, licorice extract, crystalline cellulose, Kaoliang color, and guar gum, and mixed preparations such as L-sodium glutamine preparations, alkali agents for noodles, preservative formulations, and tar color formulations.

The food composition of the present invention may include the compound of Formula 1 or a sitologically acceptable salt thereof in an amount of 0.01 wt % to 95 wt %, preferably 1 wt % to 80 wt %, based on a total weight of the composition. Furthermore, the compound of Formula 1 or a sitologically acceptable salt thereof contained in the food composition of the present invention may be obtained by a method identical or similar to the extraction method described above in the preparation of the pharmaceutical composition, without being limited thereto.

In addition, the food composition of the present invention may be prepared and processed in the form of tablets, capsules, powders, granules, liquids, and pills for the purpose of preventing or alleviating the neurodegenerative disorder.

For example, the health functional food in the form of a tablet may be prepared by granulating a mixture of the compound of Formula 1 or a sitologically acceptable salt thereof, an excipient, a binder, a disintegrant, and other additives, and compression molding the granulated mixture using a lubricant or directly compression molding the granulated mixture. Also, the health functional food in the form of a tablet may include a flavor enhancer, if necessary, and may be coated with an appropriate coating agent, if necessary.

Among the health functional food in the form of a capsule, hard capsules may be prepared by filling common hard capsules with a powdered mixture of the compound of Formula 1 or a sitologically acceptable salt thereof and an additive such as an excipient, or granules thereof or coated granules. Soft capsules may be prepared by filling a capsule base such as gelatin with a mixture of the compound of Formula 1 or a sitologically acceptable salt thereof and an additive such as an excipient. The soft capsules may include a plasticizer such as glycerin or sorbitol, a colorant, a preservative, and the like, if necessary.

The health functional food in the form of pills may be prepared by molding a mixture of the compound of Formula 1 or a sitologically acceptable salt thereof, an excipient, a binder, a disintegrant, and the like using an appropriate method, and may be coated with white sugar or any appropriate coating agent or sprinkled with starch, talc, or any appropriate substance, if necessary.

The health functional food in the form of granules may be prepared by forming a mixture of the compound of Formula 1 or a sitologically acceptable salt thereof, an excipient, a binder, a disintegrant, and the like in a granular form using an appropriate method, and may include a flavoring agent or a flavor enhancer, if necessary. The health functional food in the form of granules may be prepared using sieves No. 12 (1680 μm), No. 14 (1410 μm), and No. 45 (350 μm) such that all of the granules pass sieve No. 12, an amount of the granules remaining on sieve No. 14 is 5.0% or less of the total amount of the granules, and an amount of the granules passing sieve No. 45 is 15.0% or less of the total amount of the granules.

Definitions of the terms excipient, binder, disintegrant, lubricant, flavor enhancer, and flavoring agent are described in references well known in the art and include those having the same or similar function (*Handbook of the Korean pharmacopoeia*, MoonSung Co., Korean Association of Pharmacy Education, 5th edition, pp. 33-48, 1989).

Another aspect of the present invention provides a feed composition for preventing or alleviating a neurodegenerative disorder including the compound of Formula 1 or a sitologically acceptable salt as an active ingredient.

[Formula 1]

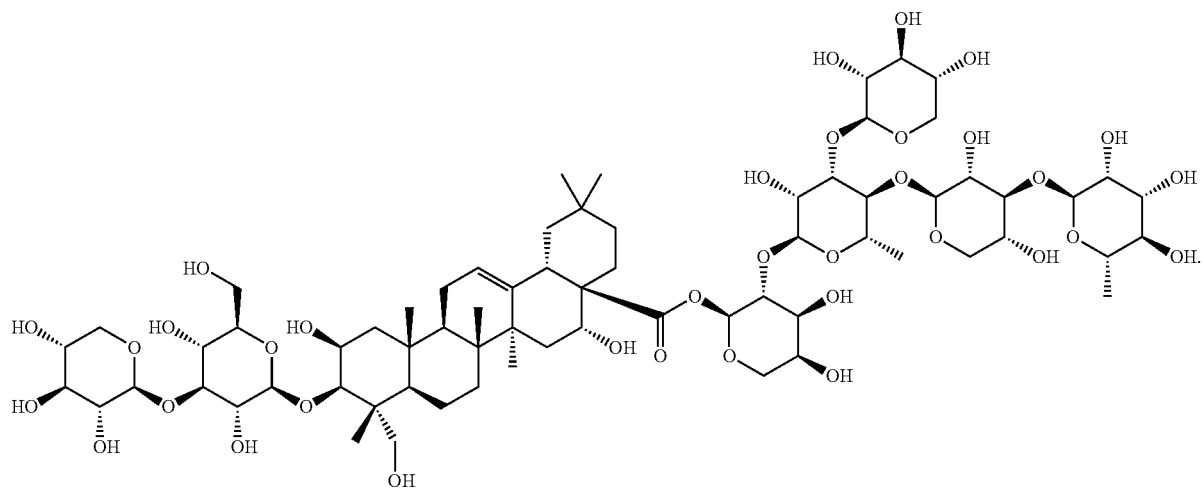

In this regard, definitions of the sitologically acceptable salt, neurodegenerative disorder, prevention, and alleviation are as described above.

As used herein, the term "feed" refers to food for animals to eat, specifically a substance that supplies organic or inorganic nutrients necessary for maintaining the animals' lives or produce meats, milk, and the like. The feed may include a feed additive and may be prepared in various forms well known in the art.

A composition including the compound of Formula 1 of the present invention or a sitologically acceptable salt thereof may be used to prevent the outbreak of Parkinson's disease or treat the disease in individuals other than humans such as livestock or companion animals, and may be used as a functional feed additive or a feed composition.

An amount of the compound of Formula 1 or a sitologically acceptable salt thereof in the feed composition according to the present invention may be appropriately adjusted according to the type and age of the livestock to be treated, application form, desired effects, and the like, for example, in the range of 1 wt % to 99 wt %, preferably 10 wt % to 90 wt %, more preferably 20 wt % to 80 wt %, without being limited thereto.

The type of the feed is not particularly limited, and any feed commonly available in the art may be used. Non-limiting examples of the feed may include: vegetable feeds such as grains, root-plants, food-processing by-products, algae, fibers, fats and oils, starches, Cucurbitaceae vegetables, or grain by-products; and animal feeds such as proteins, inorganic substances, fats and oils, minerals, single-cell proteins, animal plankton, or foods. These feeds may be used alone or in a combination of at least two thereof.

Alternatively, the compound of the present invention or a sitologically acceptable salt thereof may be used as a feed additive added to the feed composition. The feed additive may be a substance added for improving productivity or a health condition of target animals, without being limited thereto. The feed additive may be an auxiliary feed under the Control of Livestock and Fish Feed Act.

The feed additive of the present invention may further include at least one component selected from an organic acid such as citric acid, fumaric acid, adipic acid, and lactic acid or a natural antioxidant such as polyphenol, catechin, tocopherol, vitamin C, green tea extract, chitosan, and tannic acid, and may further include any other additive such as a buffer or a bacteriostatic agent, if necessary. Also, if necessary, the feed additive may be prepared in liquids, capsules, granules, or tablets.

The feed or feed additive may further include substances having various effects such as supplementing nutrients and preventing weight loss, enhancing digestibility of fibers in the feed, improving milk quality, preventing reproductive disorders and improving conception rates, or preventing high-temperature stress in summer. For example, the feed or feed additive may also be used with a nutritional supplement, a growth promoter, a digestive and absorption enhancer, and a disease-preventing agent in addition to main various supplements such as amino acids, minerals, vitamins, antioxidants, anti-fungal agents, and microbial agents, and main ingredients such as vegetable protein feeds such as crushed or pulverized wheat, barley, and corn, animal protein feeds such as powdered blood, powdered meat, and powdered fish, or animal and vegetable fats.

The feed additive of the present invention may be fed to a number of animals including mammals and poultry. For example, in order to maintain or improve appearance, the feed and feed additive may be used for livestock such as cattle and goats and pets such as dogs and cats, without being limited thereto.

Advantageous Effects

Since the novel triterpene saponin derivative, astersaponin I (Compound 1), of the present invention increases the expression level of LC3 protein, which is a membrane protein of autophagosomes in brain cells, it may be effectively used to prevent or treat a neurodegenerative disorder via autophagy-inducing action.

BRIEF DESCRIPTION OF DRAWINGS

FIG. 24A shows typical absorbance bands and relative densities of autophagy-related protein markers including LC3, p62, AMPK, Erk, ULK, and mTOR in ST. FIG. 24B shows typical absorbance bands and relative densities of autophagy-related protein markers including LC3, p62, AMPK, Erk, ULK, and mTOR in SN. Data are expressed as mean±SEM (n=5). *p<0.05, p<0.01, *p<0.001 significant difference from control, #p<0.05, ##p<0.01, ###p<0.01 significant difference from MPTP-treated group.

BEST MODE

Figure 1:
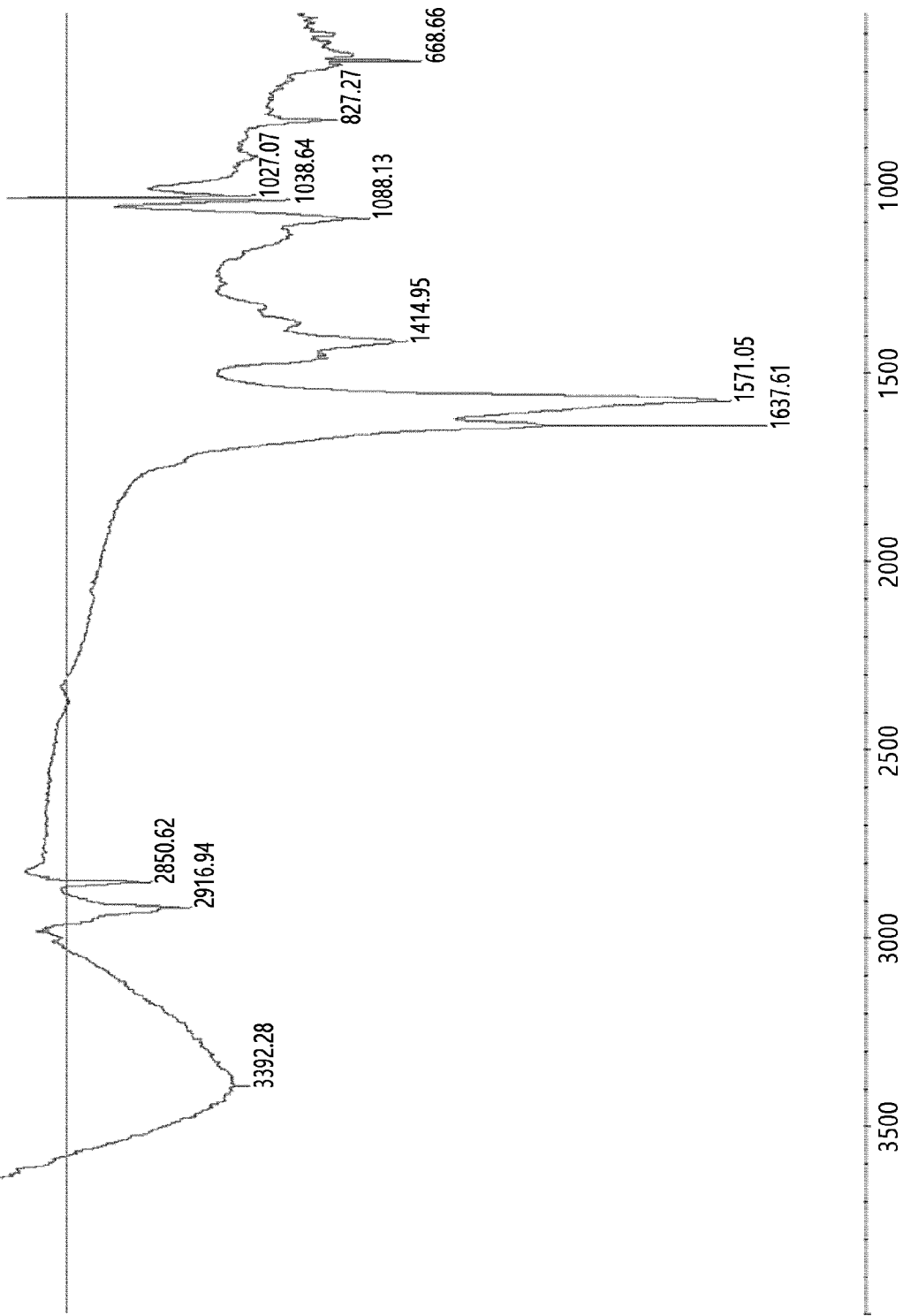
FIG. 1 is an IR spectrum of a compound (astersaponin I, Compound 1) isolated and identified according to an embodiment of the present invention.

Hereinafter, the present invention will be described in more detail with reference to the following examples. However, the following experimental examples are merely presented to exemplify the present invention, and the scope of the present invention is not limited thereto.

Experimental Procedure

Optical rotations were acquired with a Perkin-Elmer (Waltham, Mass., USA) 343 polarimeter. UV and IR spectra were acquired with a Perkin-Elmer Lambda 35 spectrophotometer and a Thermo (Waltham, Mass., USA) iS50 spectrometer. Electron circular dichroism (ECD) spectra were obtained with an Applied Photophysics (Leatherhead, England) Chirascan V100 spectrometer. NMR spectra were recorded on Varian (Palo Alto, Calif., USA) 500 MHz, Joel (Tokyo, Japan) 600 MHz, and Bruker (Billerica, Mass., USA) 850 MHz NMR spectrometers. High-resolution mass spectrometry (HRMS) data were collected on a Thermo Q-Exactive mass spectrometer. Preparative HPLC system utilized YMC (Kyoto, Japan) LC-Forte/R and an ELS detector with a Phenomenex Luna C18 column (10 μm, 250 mm×21.2 mm). Column chromatography was carried out using GE Healthcare (Chicago, Ill., USA) Sephadex LH-20 gel.

<Plant Materials>

The whole plant of *Aster koraiensis* was collected in October 2016 after cultivation at Pyeongchang Wild Plant Nursery and Farming Corporation (Pyeongchang, Republic of Korea). A voucher specimen (No. BS0083A1) was deposited in the Korea Institute of Science and Technology Gangneung Institute.

<Substance>

Dulbecco's modified Eagle's medium (DMEM), fetal bovine serum (FBS), 100 units/mL penicillin, and 100 mg/mL streptomycin were purchased from Gibco (Thermo Fisher Scientific). 1-Methyl-4-phenyl-1,2,3,6-tetrahydropyridine (MPTP) hydrochloride, 1-methyl-4-phenylpyridinium ($MPP^+$) iodide, 3-methyladenine (3-MA), and ropinirole were purchased from Sigma Chemical Co. (St. Louis, Mo., USA). Wortmannin (Wart) and bafilomycin A1 (Baf) were purchased from Abcam (MA, USA). Anti-glyceraldehyde-3-phosphate dehydrogenase (GAPDH), anti-AMPK, anti-phosphorylated AMPK (p-AMPK), anti-ULK, anti-phosphorylated ULK555 (p-ULK555), anti-Erk, anti-phosphorylated Erk (p-Erk), anti-mTOR, anti-phosphorylated mTOR (p-mTOR), anti-LC3B, anti-tyrosine hydroxylase (TH), rabbit-derived anti-α-synuclein primary antibody, anti-rabbit horseradish peroxidase-conjugated IgG secondary antibody, Erk inhibitor U0126, AMPK siRNA, and AMPK siRNA control were purchased from Cell Signaling Technology (Boston, Mass., USA). An autophagy tandem RFP-GFP-LC3B kit was purchased from Thermo Fisher Scientific (MA, USA). An MTT assay kit (Z-Cytox) was purchased from DAEILLAB Co, Ltd, Seoul, Republic of Korea. A dopamine ELISA kit was purchased from Abnova (Taipei City, Taiwan), and a MAO-B assay kit was supplied by Promega (Woods Hollow Road, Madison, Wis., USA). All reagents of the highest grades were used and selected from commercially available products.

Preparation Example 1: Cell Cultivation

Human neuroblastoma (SH-SY5Y) cells were purchased from the American Type Culture Collection (Manassas, Va., USA) and cultured in DMEM supplemented with 10% heat-inactivated FBS and 1% penicillin/streptomycin. The SH-SY5Y cells were cultured at 37° C. in a humid atmosphere containing 5% $CO_2$. First, the cells were seeded on a 6-well plate at a density of $80 \times 10^4$ cells/well with 2 mL of the culture medium followed by, after 24 hours, treatment with samples (AKNS EtOH extract, an AKNS n-BuOH fraction, or AKNS-2) having desired concentrations. For conditions of the presence of 3-MA, Wart, Baf, or U0126, the cells were treated with these reagents for 30 minutes before treating the cells with the samples. The SH-SY5Y cells were transfected with AMPK siRNA and then administered with AKNS-2 at 36 hours after siRNA transfection. When $MPP^+$ treatment is needed, after 1 hour from treatment with the samples, the cells were treated with $MPP^+$. After 24 hours from treatment with the samples, the SH-SY5Y cells were recovered and used for subsequent analysis.

Experimental Example 1: MTT Assay to Measure Cell Viability

Cell viability was detected using an MTT assay kit (Z-Cytox). Briefly, the SH-SY5Y cells were seeded on a 96-well plate at a density of $2 \times 10^4$ cells/well with 100 μL of a culture medium. After 24 hours, the SH-SY5Y cells were treated with AKNS-2 and/or $MPP^+$ having desired concentrations to identify cytotoxicity of AKNS-2 and $MPP^+$. After 24 hours, 10 μL of the MTT reagent was added to each well of the 96-well plate including the cells. Absorbance was measured at 450 nm using a microplate spectrophotometer (BioTek, Vt., USA). In order to prove protective effects of AKNS-2 against cytotoxicity induced by $MPP^+$, the cells were treated with 2 mM $MPP^+$ at 1 hour after the AKNS-2 treatment. The next day, absorbance was measured at 1 hour after adding the MTT reagent thereto. In order to identify whether AKNS-2 has protective effects against $MPP^+$-induced cytotoxicity by inducing autophagy, SH-SY5Y cells were treated with U0126 or AMPK siRNA and AKNS-2 (5 μM and 10 μM) was added to the cells after 30 minutes and 36 hours, respectively. At 1 hour after the AKNS-2 treatment, 2 mM $MPP^+$ was added to the cells.

Experimental Example 2: Measurement of RFP-GFP-LC3 by Fluorophotometry

SH-SY5Y cells were cultured in a 24-well plate at a density of $8 \times 10^4$ cells/well on a glass cover slip. Transfection was performed in accordance with guidelines of the autophagy tandem RFP-GFP-LC3B kit. After culturing the cells for 24 hours, the cells were treated with an LC3B reagent. After the transfected cells were incubated for 24 hours, 50 nM Wart or 100 nM Baf was administered thereto, and then AKNS-2 (10 μM) was added thereto. The cells were immobilized with 4% paraformaldehyde and permeabilized with 0.1% Triton X100. Nuclei thereof were stained with 4,6-diamidino-2-phenylindole (DAPI, 25 μg/mL). Fluorescent signals were detected using a confocal microscope (Leica, Solms, Germany).

Preparation Example 2: Preparation of Cell Lysates

At 24 hours after drug treatment, the culture medium was removed from the 6-well plate, and the cells were gently washed once with cold saline. Subsequently, 1 mL of cold saline was added to each well, and cells attached to the bottom were floated by rubbing the bottom with a 1 mL pipette. The suspension was collected in a 1.5 mL tube and centrifuged at 4° C. at 13000×g for 5 minutes. After removing a supernatant, 50 μL of a RIPA lysis buffer including a protease inhibitor cocktail (Roche, Mannheim, Germany) and purchased from Cell Signaling Technology (Danvers, Mass., USA) was added to the cell pellet. After shaking the mixture at 4° C. for 30 minutes, the obtained cells were centrifuged at 4° C. at 13000×g for 20 minutes. A supernatant was collected therefrom, and a concentration of proteins was measured using a standard curve constructed using BSA by the Bradford method. Then, the supernatant was diluted with a loading buffer and heated at 99° C. for 5 minutes. Resultant cells were used in a subsequent western blot analysis.

Preparation Example 3: Animal Test

In this study, all animal management and experimental protocols were performed in compliance with guidelines of the Institutional Animal Care and Use Committee of the Korea Institute of Science and Technology. 40 mice (C57BL/6j, male, 8 weeks old) were purchased from SLC Inc. (Shizuoka, Japan). After arrival, every four mice were hosed in each cage (30 cm×18.5 cm×13 cm) and allowed free access to feed and water. All mice were housed under the following constant conditions: lights on from 6:00 to 18:00, a temperature of 23° C.±1° C., and a humidity of 50%±10%. After 7 days of a habituation period, the mice were used in the experiments according to standard protocols.

Figure 22:
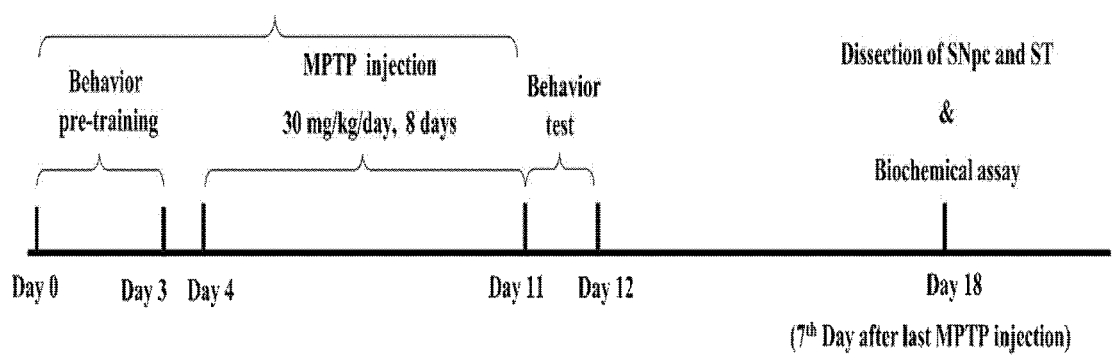
FIG. 22 shows protective effects of AKNS-2 on behavior performance of MPTP-damaged animals. (A) shows a schematic diagram of a sub-chronic in vivo PD model induced by administration of MPTP. Mice were pre-trained for 3 days using a rotarod, a pole, and a wire. After the last MPTP administration, behavior performance of the mice was recorded at different time points. (B), (C), and (D) show behavior performance of mice measured in the rotarod, pole, and wire hanging tests at different time points before and after administration of MPTP. Data are expressed as mean±SEM (n=5). p<0.01, *p<0.001 significant difference from control, #p<0.05, ##p<0.01, ###p<0.001 significant difference from MPTP-treated group.
Figure 22:
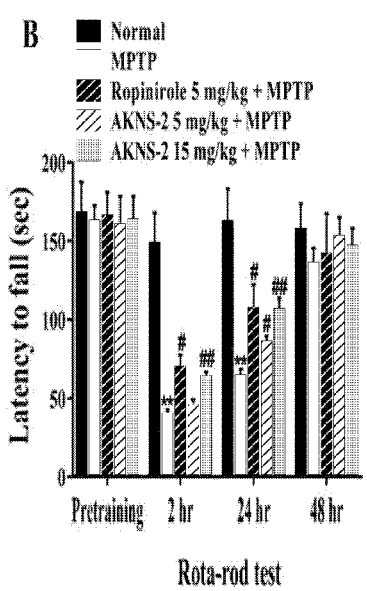
Figure 22:
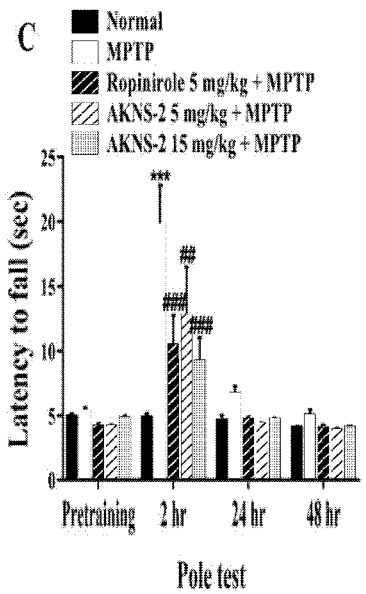
Figure 22:
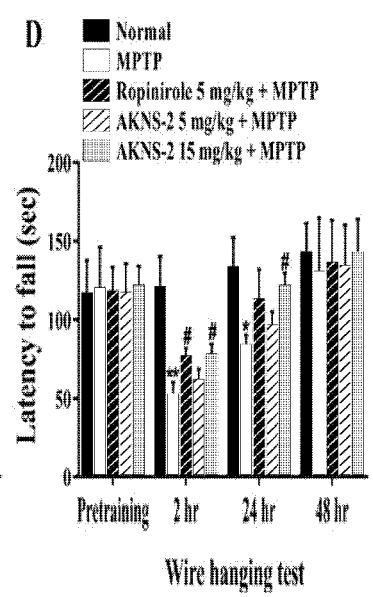

Preparation Example 4: Animal Classification and Sample Treatment 40 mice were classified into five groups such that eight mice belonged to each group. After the habituation period, all mice were orally administered with a drug every day. While the mice of Groups 1 and 2 were administered with saline (p.o.), the mice of Groups 3, 4, and 5 were administered with 5 mg/kg ropinirole (p.o.), 5 mg/kg AKNS-2 (p.o.), and 15 mg/kg AKNS-2 (p.o.), respectively. From the 5th day therefrom, the mice of Group 1 were intraperitoneally administered with a saline at 1 hour after gavage feeding of saline, and the mice of Groups 2, 3, 4, and 5 were administered with 30 mg/kg MPTP (i.p.) at 1 hour after gavage feeding of saline, ropinirole, AKNS-2 (5 mg/kg), and AKNS-2 (15 mg/kg), respectively. Each mouse was administered with a single dose of saline/MPTP injection every day for 8 days. At 7 days after the final MPTP injection, all mice were sacrificed by cervical dislocation, and then the whole brain, SNpc, and striatum (ST) were excised for biochemical analysis. FIG. 22 shows a schematic diagram of an animal test.

Experimental Example 3: Rotarod Test

A rotarod test was performed according to a known method with minimal modification (Borlongan C. V. et al., *Pharmacology Biochemistry and Behavior.* 1995, 52:225; Hu X. et al., *Neuropharmacology,* 2017, 117:352). Briefly, the test consisted of a pretraining section and a test section. The pretraining section was performed for consecutive 4 days. The mice were positioned in a cylinder of a rotarod apparatus such that tails of all mice faced an operator and trained for 300 seconds at a constant speed of 16 rpm. During the 300 seconds, mice falling to the floor were placed back on the cylinder by the operator. All mice were trained three times in total every day at an interval of about 30 minutes before administration of MPTP. The mice were treated with a single dose of 30 mg/kg MPTP at 1 hour after administration of AKNS-2 (5 mg/kg and 15 mg/kg) for consecutive 8 days starting on the next day of the last day of behavioral training. Latency to fall off the rotarod was recorded for each mouse. In the test section, performance of all mice was tested on the rotarod according to protocols applied during the pretraining section at three time points, i.e., 2 hours, 24 hours, and 48 hours after the last administration of MPTP. Latency to fall off the rotarod was measured for each mouse. Only mice that stayed on the cylinder for 60 seconds or more in the pretraining section were used for statistical analysis. An average time of three tests was calculated to evaluate balance, grip strength, and motor coordination.

Experimental Example 4: Pole Test

A pole test was performed according to a known method with minimal modification (Choi D. Y. et al., *Neurobiology of Disease,* 2013, 49:159). Briefly, on the day before MPTP administration, a wood pole (50 cm in length and 1 cm in diameter) with a rough surface was placed in a sound-proof chamber. Each mouse was placed on the top of the pole with the head raised up, and a time taken for the mouse to turn and descend the pole was recorded up to 120 seconds with a stopwatch. The same training was performed three times at an interval of 30 minutes. Performance of all mice on the pole was tested according to protocols applied during the pretraining section at three time points, i.e., 2 hours, 24 hours, and 48 hours after the last administration of MPTP. An average time of three tests was calculated to evaluate motor function.

Experimental Example 5: Wire Hanging Test

A wire hanging test was performed according to a known method with minimal modification (Zhu W. et al., *Brain, Behavior, and Immunity,* 2018, 69: 568). Briefly, a horizontal wire (1.5 mm in diameter, 50 cm in length, and 30 cm above a bedding material) was fixed between two poles. Fluffy bedding was placed under the wire. Each mouse was handled with its tail such that the mouse held the center of the wire with its front paws. Immediately after the mouse properly floated, a timer was started. A time taken for the mouse to fall off the wire was recorded up to 300 seconds. On the day before MPTP administration, the test was performed three times for each mouse, and an average hanging time of three tests was analyzed as an index to evaluate balance, myofunction, and coordination. Performance of all mice on the wire hanging test was tested at three time points, i.e., 2 hours, 24 hours, and 48 hours after the administration of MPTP. Average latency to fall off the wire onto the bedding material was calculated for each mouse.

Preparation Example 5: Preparation of Brain Tissue of Mouse

On the $7^{th}$ day after the last administration of MPTP, SNpc and ST of each mouse were carefully excised and stored at −80° C. until use. Thereafter, brain tissue of SNpc and ST was homogenized in a PRO-PREP™ lysis buffer (iNtRON, Gyeonggi, Korea) containing a phosphatase inhibitor cocktail set I (Sigma-Aldrich, Mo., USA). After shaking at 4° C. for 30 minutes, homogenates were centrifuged at 4° C. at 13000×g for 20 minutes, and a supernatant obtained therefrom was collected and added to a new 1.5 mL tube. A concentration of proteins contained in the supernatant was measured by the Bradford method. A part of the supernatant was mixed with the same volume of a loading buffer and denatured in a heater at 99° C. for 5 minutes for western blot analysis. The remaining supernatant was stored at −80° C. for subsequent tests for MAO-B activity and DA level using an ELISA kit.

Experimental Example 6: Measurement of DA Level

DA levels in ST were measured using a competitive ELISA kit (Abnova, Taipei City, Taiwan) according to the manufacturer's instructions. Briefly, ST was homogenized in 0.01 N HCl in the presence of EDTA and sodium metabisulfite. Homogenates were centrifuged at 13000×g for 5 minutes. A supernatant was collected therefrom and used to measure DA levels. After determining a concentration of proteins contained in the supernatant, the DA level in each brain sample was detected twice using the ELISA kit. Absorbance was measured using a microreader (BioTek, Vt., USA) at 450 nm, and the intensity was inversely proportional to the DA level. The DA level was expressed as ng/mg protein.

Experimental Example 7: Determination of MAO-B Activity

A MAO-B assay kit of Promega Corporation (Woods Hollow Road, Madison, Wis., USA) was used to determine MAO-B activity of ST and SN according to the manufacturer's instructions. In order to detect MAO activity, the kit was used according to a homogeneous luminescent method. The assay includes two steps. First, a MAO-B substrate was added to a MAO-B enzyme-containing substance (ST and SN samples) to produce methyl ester luciferin. Next, the produced methyl ester luciferin was reacted with esterase and luciferase to generate light. MAO-B activity was directly proportional to an amount of generated light. Luminescence signals were measured using an Infinite M1000 multimode microplate reader (TECAN, Männedorf, Switzerland). MAO-B activity was expressed as relative light unit (RLU)/mg protein).

Experimental Example 8: Western Blot Analysis

Protein markers contained in lysates of the SH-SY5Y cells and brain tissue of the mice (SNpc and ST) were measured by western blot analysis. Briefly, after determining a concentration, a protein sample (20 μg) was separated by 8%, 10%, or 15% sodium dodecyl sulfate-polyacrylamide gel electrophoresis (SDS-PAGE). Then, proteins separated on the gel were transferred to a polyvinylidene fluoride (PVDF) membrane for 45 minutes using a Trans-Blot Turbo Transfer System (Bio-Rad, USA). The membrane was washed with tris-buffered saline with 0.1% Tween 20, TBST) for 5 minutes and then blocked by 5% skim milk dissolved in a TBST buffer. The membrane was further incubated with monoclonal primary antibodies derived from rabbits (anti-GAPDH, anti-AMPK, anti-p-AMPK, anti-ULK, anti-p-ULK555, anti-Erk, anti-p-Erk, anti-mTOR, anti-p-mTOR, anti-LC3B, anti-TH, and anti-α-synuclein antibodies). The primary antibodies were diluted in a blocking buffer at a ratio of 1:1000 and incubated overnight at 4° C. On the second day, the membrane was washed with TBST three times (10 minutes each) and incubated at room temperature in a horseradish peroxidase-conjugated goat anti-rabbit IgG secondary antibody (diluted in a blocking buffer at a ratio of 1:2000). After incubating in the secondary antibody for 1 hour, the membrane was washed for 30 minutes. The protein blots on the membrane were developed using an ECL detection kit and visualized using an LAS-4000 mini system (Fujifilm, Japan). The intensity of the protein blots was quantified using Multi Gauge software (Fujifilm, Japan).

Experimental Example 9: Statistical Analysis

In the present invention, all data were analyzed with GraphPad Prism 7 Software (CA, USA) and expressed as mean±SEM. Statistical analysis was performed using a one-way analysis of variance (ANOVA) or Student's t-test. A p-value of less than 0.05 was regarded as statistically significant.

Example 1: Extraction, Isolation, and Identification

Dried *Aster koraiensis* (*A. koraiensis*, 15 kg) was ground and extracted with 95% ethanol at 65° C. for 3 hours. The extracted solution was evaporated in a vacuum to obtain a powdered extract (1.7 kg, yield: 11.3%). Subsequently, the extract was subjected to fractionation using n-hexane, ethyl acetate, and n-butanol to obtain three types of fractions (149 g, 175 g, and 190 g, respectively). According to biological evaluation, n-butanol fraction (1.4 g) was chromatographed using preparative HPLC under isocratic conditions ($CH_3CN/H_2O$, 7:18, flow rate: 10.0 mL/min) to obtain a bioactive fraction ($t_R$=33.0 min). The obtained fraction was separated on a Sephadex LH-20 column (2.8 cm×100 cm, $CH_3OH$, flow rate: 0.25 mL/min) to obtain astersaponin I (Compound 1, 34.6 mg, $t_R$=800 min).

White powder;
$[\alpha]^{20}_D$ −18.0 (c 0.01, $CH_3OH$);
IR $u_{max}$ (ATR) 3392, 2916, 2850, 1637, 1571, 1416, 1088 $cm^{-1}$,
ECD (c 0.1 mM, $CH_3CN$) Δε+3.1 (203);
$^1H$ and $^{13}C$ NMR, See Table 1-1 and 1-2 below;
HRESIMS m/z 1487.68823 $[M+H]^+$ (calcd for $C_{68}H_{111}O_{35}$, 1487.69004).

TABLE 1-1

| Position | $\delta_C$ | $\delta_H$ (J in Hz) Aglycone | Intensities | Position | | $\delta_C$ | $\delta_H$ (J in Hz) Sugar moiety |
|---|---|---|---|---|---|---|---|
| 1 | 44.6 | 2.09(dd)J = 14.0 Hz, 2.0 Hz | 2H | Glc | 1' | 105.3 | 4.49(d)J = 7.5 Hz |
|   |      | 1.18(dd)J = 14.0 Hz, 3.5 Hz |    |     | 2' | 74.7  | 3.48(m) |
| 2 | 71.3 | 4.33(m) | 1H | | 3' | 88.1 | 3.52(m) |
| 3 | 84.2 | 3.63(m) | 1H | | 4' | 71.1 | 3.51(m) |
| 4 | 43.3 |  |  | | 5' | 77.5 | 3.31(m) |
| 5 | 48.5 | 1.33(m) | 1H | | 6' | 62.3 | 3.81(m) |
| 6 | 18.9 | 1.50(m) | 2H | |    |      | 3.71(m) |
| 7 | 34.0 | 1.67(m) | 2H | XylI | 1" | 106.2 | 4.51(d)J = 7.5 Hz |
|   |      | 1.35(m) |    |     | 2" | 73.2  | 3.64(m) |
| 8 | 41.0 |  | 1H | | 3" | 76.3 | 3.23(m) |
| 9 | 48.7 | 1.63(m) | 1H | | 4" | 70.2 | 3.81(m) |
| 10 | 37.7 |  |  | | 5" | 67.6 | 3.87(d)J = 11.5 Hz |
| 11 | 24.8 | 2.00, (m) | 2H | |   |      | 3.57(d)J = 11.5 Hz |
|    |      | 1.96(m) |    | Ara | 1" | 94.1 | 5.63(brd)J = 3.0 Hz |
| 12 | 123.9 | 5.38(brt)J = 3.5 Hz | 1H | | 2''' | 75.6 | 3.78(dd)J = 5.0 Hz, 3.0 Hz |
| 13 | 144.9 |  |  | | 3''' | 70.6 | 3.91(m) |
| 14 | 43.1 |  |  | | 4''' | 66.8 | 3.84(m) |
| 15 | 36.5 | 1.78(m) | 2H | | 5''' | 63.4 | 3.92(m) |
|    |      | 1.39(m) |    | |     |      | 3.49(m) |
| 16 | 74.8 | 4.49(d)J = 5.0 Hz | 1H | RhaI | 1'''' | 101.0 | 5.00(brd)J = 1.5 Hz |
| 17 | 50.5 |  |  | | 2'''' | 72.3 | 4.07(m) |

TABLE 1-1-continued

| Position | $\delta_C$ | $\delta_H$ (J in Hz) Aglycone | Intensities | Position | $\delta_C$ | $\delta_H$ (J in Hz) Sugar moiety |
|---|---|---|---|---|---|---|
| 18 | 42.3 | 3.06(brdd)J = 14.0 Hz, 4.0 Hz | 1H | 3'''' | 82.7 | 3.87(m) |
| 19 | 47.8 | 2.28(brdd)J = 14.0 Hz, 12.5 Hz | 2H | 4'''' | 78.9 | 3.69(m) |
|  |  | 1.04(brdd)J = 12.5 Hz, 3.5 Hz |  | 5'''' | 69.2 | 3.71(m) |
| 20 | 31.5 |  |  | 6'''' | 18.5 | 1.27(d)J = 6.0 Hz |

TABLE 1-2

| 21 | 36.6 | 1.93(m) | 2H XylII | 1''''' | 105.0 | 4.74(d)J = 8.0 Hz |
|---|---|---|---|---|---|---|
|  |  | 1.16(m) |  | 2''''' | 75.4 | 3.29(m) |
| 22 | 32.1 | 1.92(m) | 2H | 3''''' | 84.5 | 3.41(m) |
|  |  | 1.80(m) |  | 4''''' | 70.4 | 3.50(m) |
| 23 | 66.0 | 3.63(m) | 2H | 5''''' | 67.1 | 3.86(m) |
|  |  | 3.24(m) |  |  |  | 3.20(m) |
| 24 | 15.0 | 0.95(s) | 3H RhaII | 1'''''' | 102.8 | 5.14(brd)J = 1.5 Hz |
| 25 | 17.8 | 1.31(s) | 3H | 2'''''' | 72.4 | 3.93(m) |
| 26 | 18.2 | 0.80(s) | 3H | 3'''''' | 72.4 | 3.70(m) |
| 27 | 27.5 | 1.38(s) | 3H | 4'''''' | 74.1 | 3.40(m) |
| 28 | 177.2 |  |  | 5'''''' | 70.1 | 4.02(m) |
| 29 | 25.3 | 0.98(s) | 3H | 6'''''' | 18.0 | 1.24(d)J = 6.0 Hz |
| 30 | 33.5 | 0.89(s) | 3H XylIII | 1''''''' | 106.3 | 4.50(d)J = 7.5 Hz |
|  |  |  |  | 2''''''' | 75.4 | 3.28(m) |
|  |  |  |  | 3''''''' | 77.8 | 3.32(m) |
|  |  |  |  | 4''''''' | 71.1 | 3.50(m) |
|  |  |  |  | 5''''''' | 67.3 | 3.91(m) |
|  |  |  |  |  |  | 3.25(m) |

Figure 2:
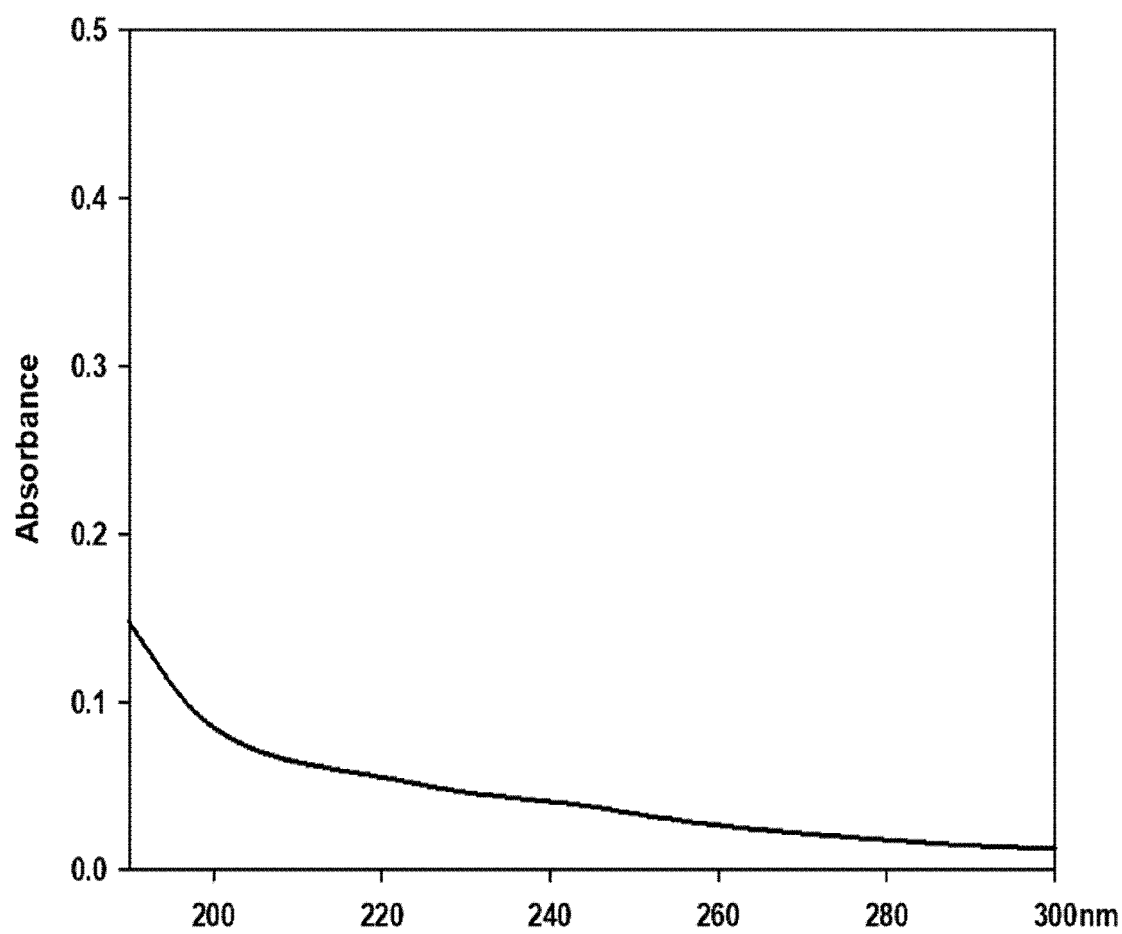
FIG. 2 is a UV spectrum of Compound 1 according to an embodiment of the present invention ($CH_3OD$).
Figure 3:
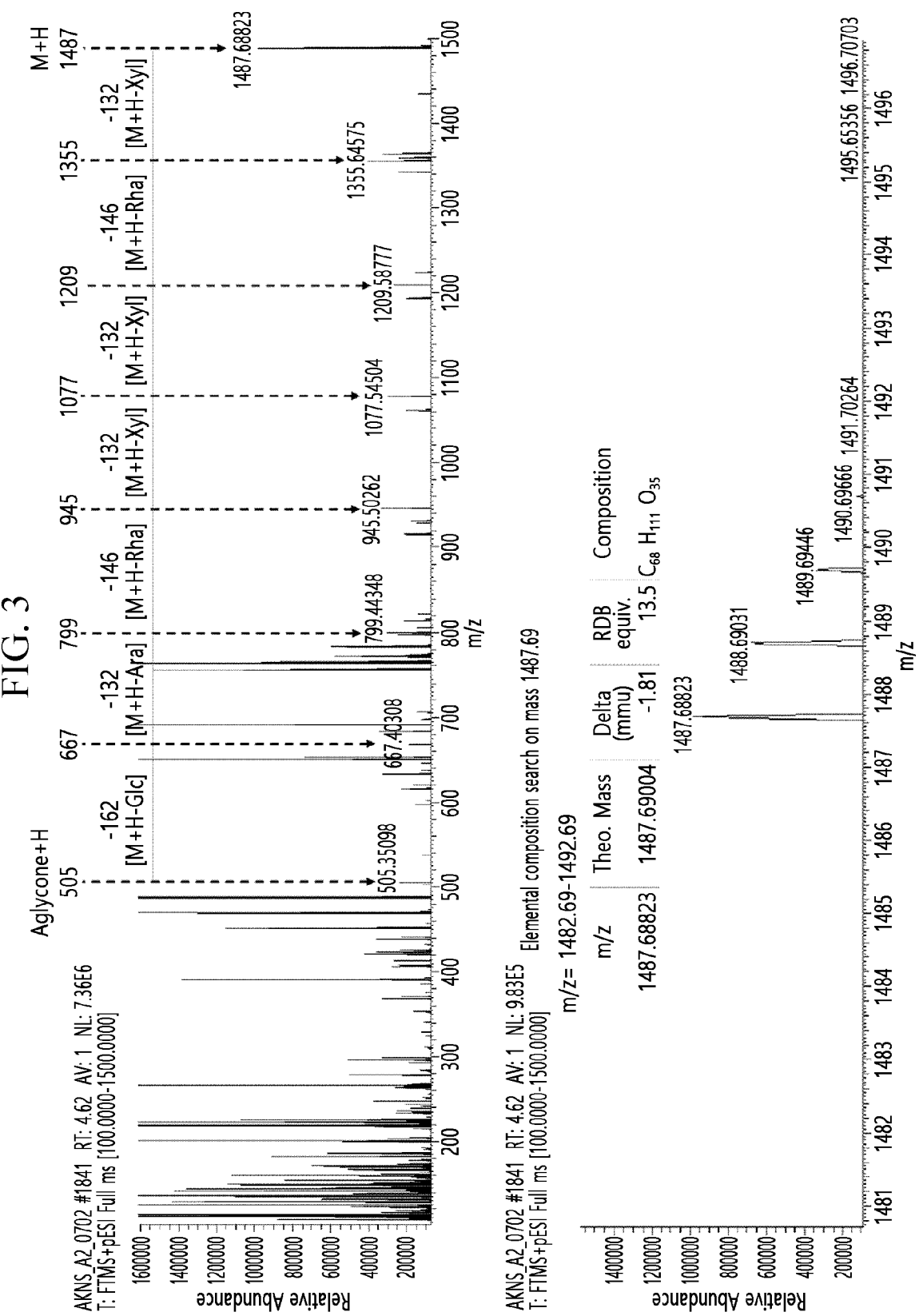
FIG. 3 is an HR-MS spectrum of Compound 1 according to an embodiment of the present invention.
Figure 4:
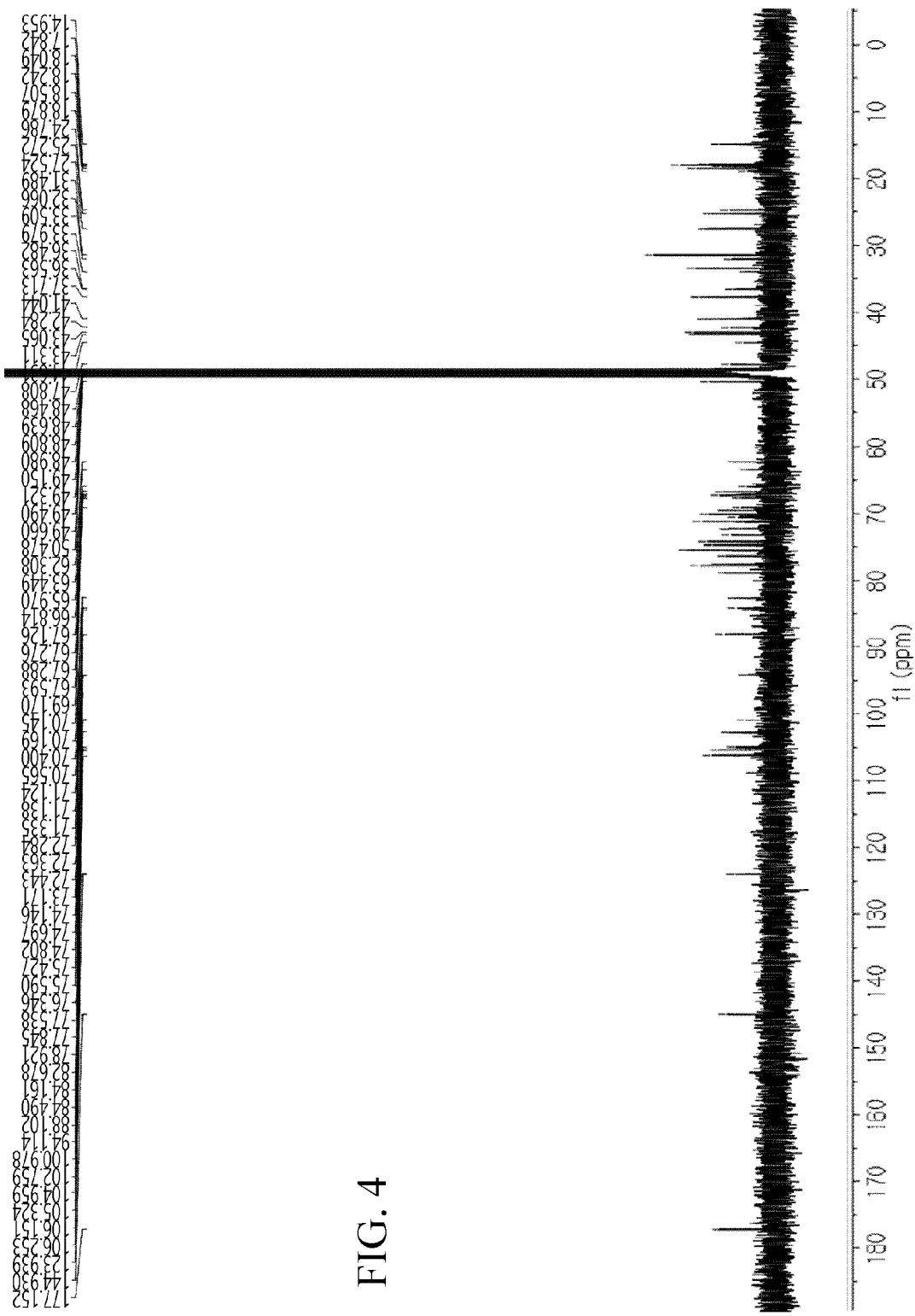
FIG. 4 is a $^{13}C$ NMR spectrum of Compound 1 according to an embodiment of the present invention (500 MHz, $CD_3OD$).
Figure 5:
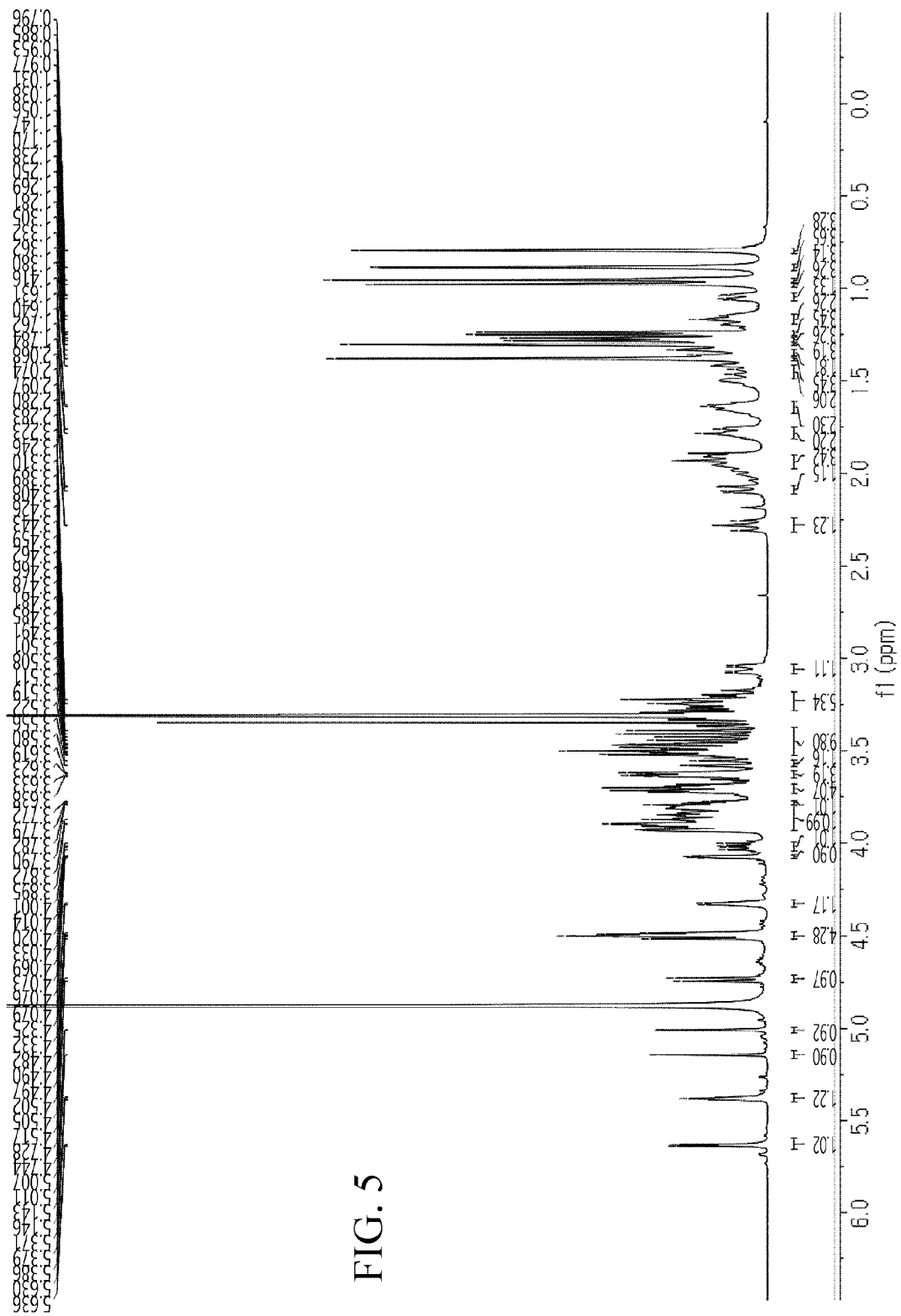
FIG. 5 is a $^1H$ NMR spectrum of Compound 1 according to an embodiment of the present invention (125 MHz, $CD_3OD$).
Figure 6:
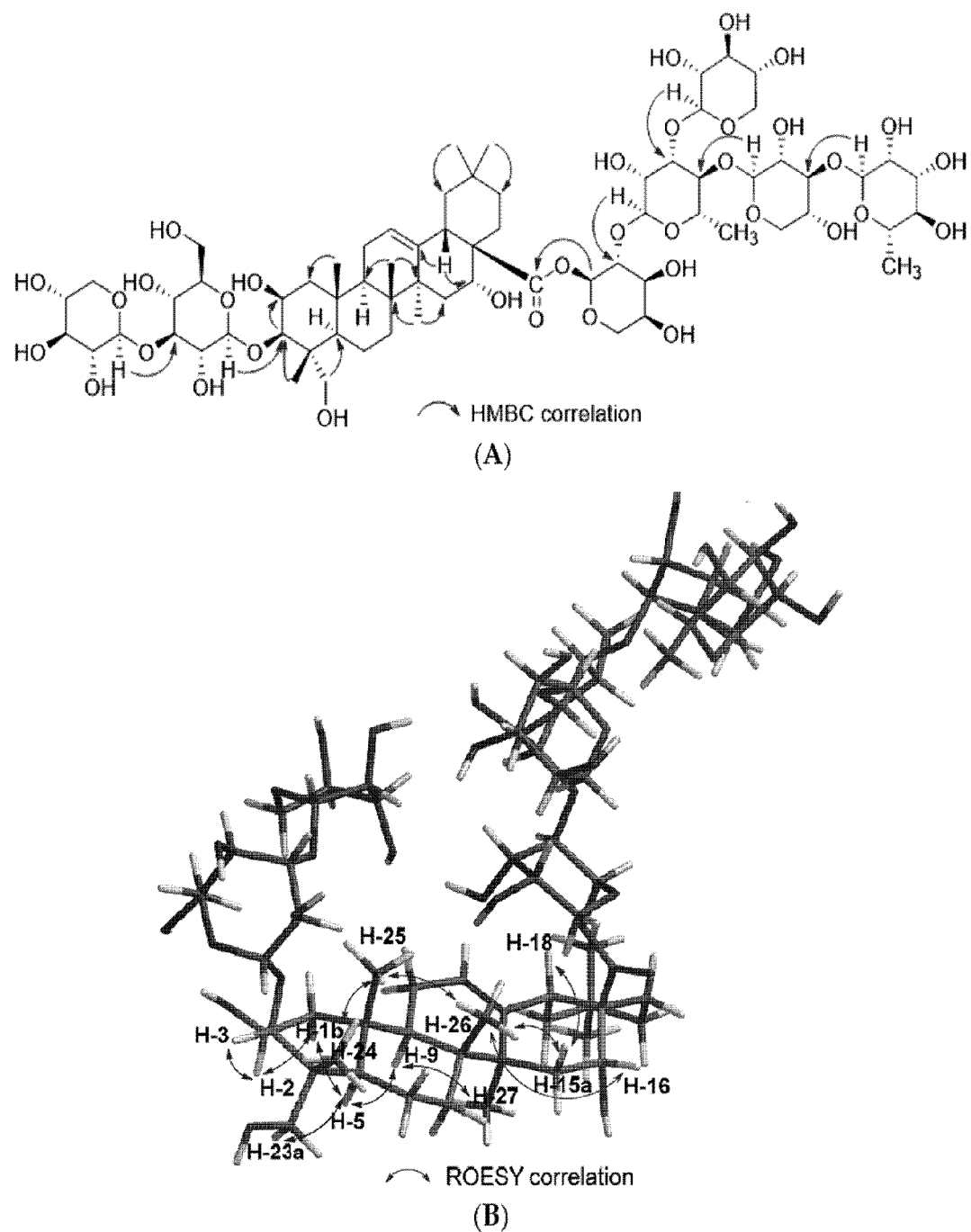
FIG. 6 shows key (A) HMBC and (B) ROSEY correlations of Compound 1 according to an embodiment of the present invention.
Figure 7:
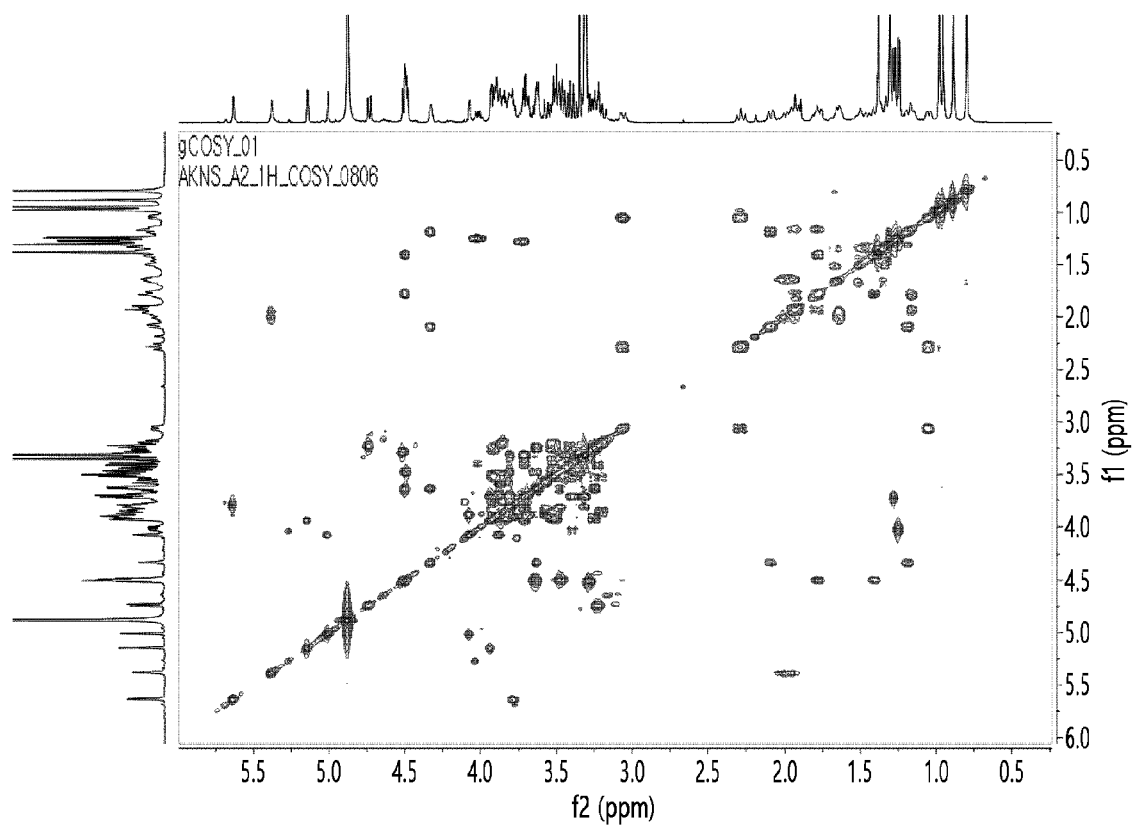
FIG. 7 is a $^1H$-$^1H$ COSY spectrum of Compound 1 according to an embodiment of the present invention (500 MHz, $CD_3OD$).
Figure 8:
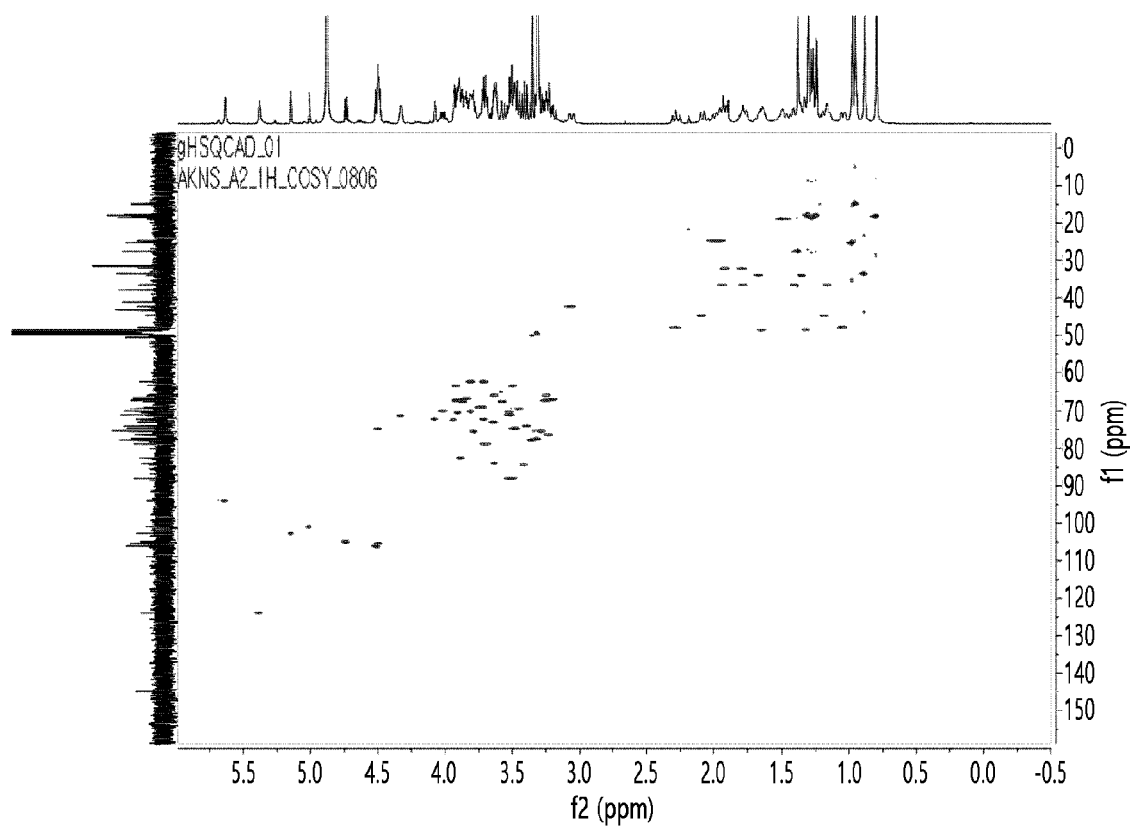
FIG. 8 is an HSQC spectrum of Compound 1 according to an embodiment of the present invention (500 MHz, $CD_3OD$).
Figure 9:
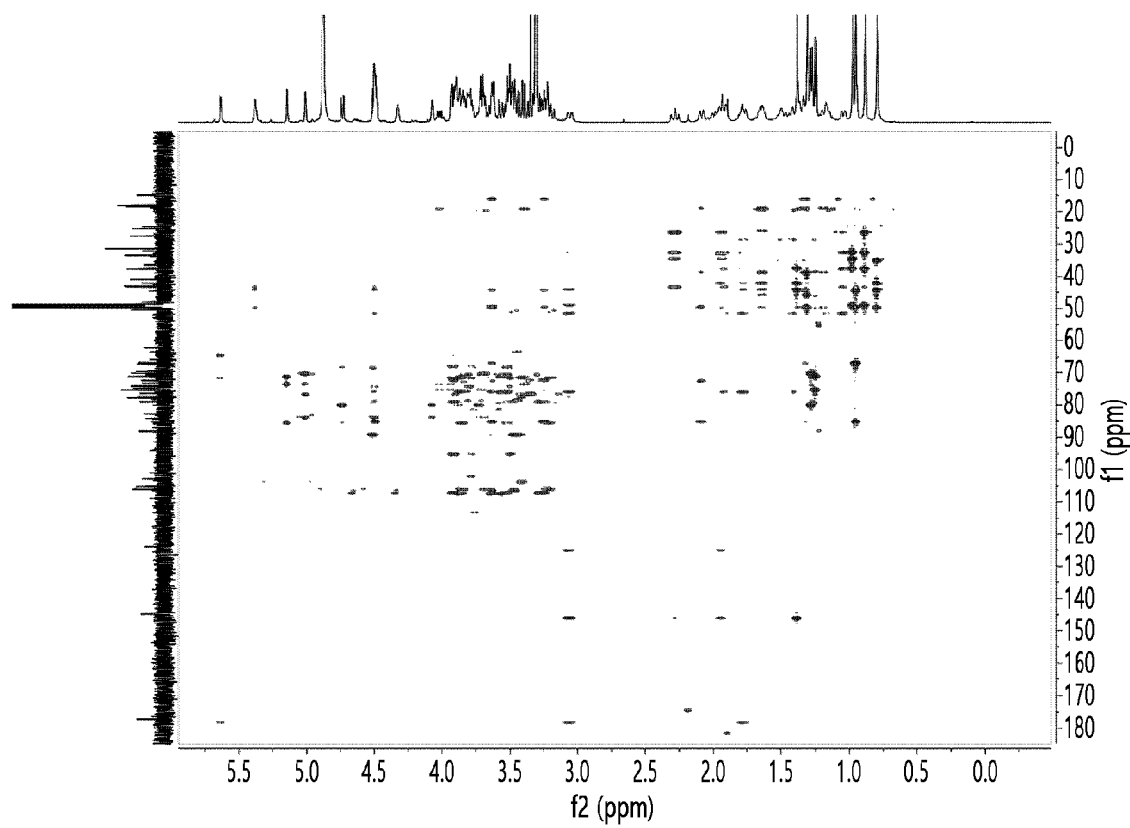
FIG. 9 is an HMBC spectrum of Compound 1 according to an embodiment of the present invention (500 MHz, $CD_3OD$).
Figure 10:
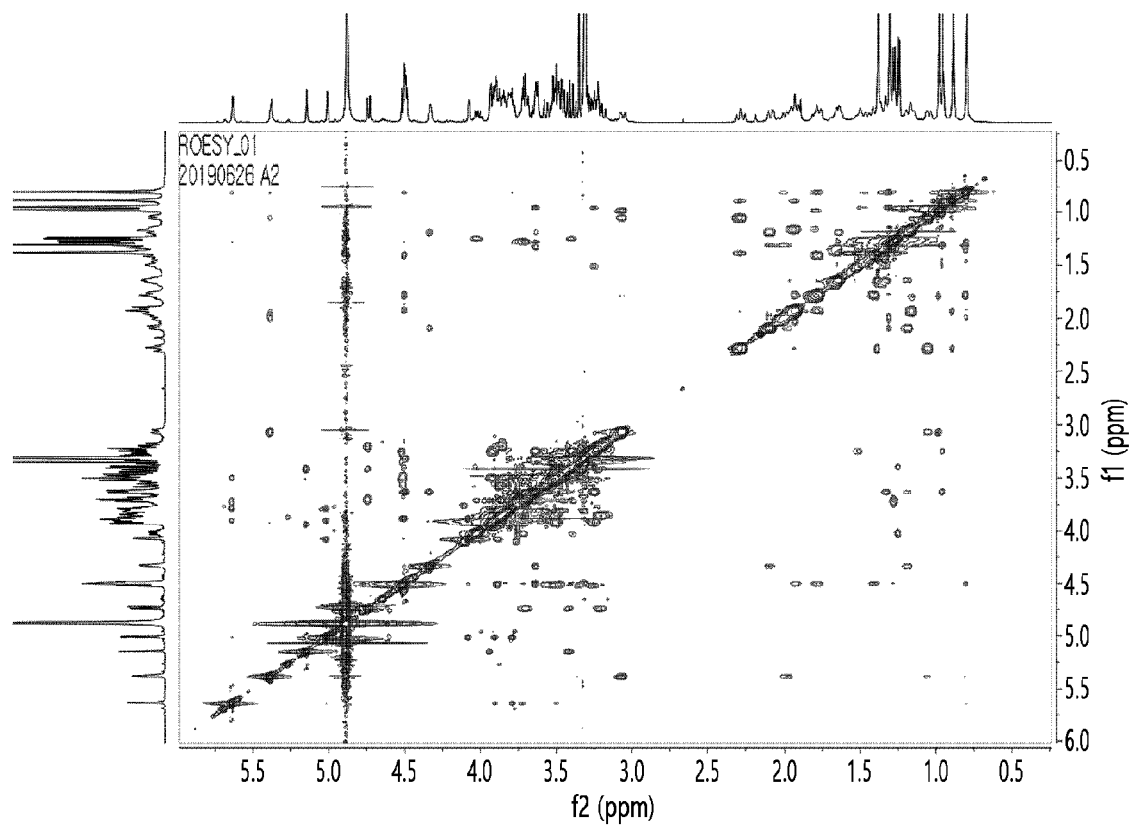
FIG. 10 is a 2D ROESY spectrum of Compound 1 according to an embodiment of the present invention (500 MHz, $CD_3OD$).

Astersaponin I was isolated as a white amorphous powder. The IR data exhibited absorbance bands at 3368 cm$^{-1}$ and 1657 cm$^{-1}$, indicating hydroxy and carbonyl groups, respectively (FIG. 1). The UV data displayed only terminal absorption at 205 nm (FIG. 2), which was attributable to terpene with little conjugation. The molecular formula was deduced to be $C_{68}H_{110}O_{35}$ on the basis of HR-MS data, and the fragmentation patterns (m/z 1487, 1355, 1209, 1077, 945, 799, 667, and 505) suggested that the triterpene aglycone was present with several sugar moieties (FIG. 3). The $^1$H and $^{13}$C NMR data exhibited characteristic signals for aglycone and sugar moieties (see Tables 1-1 and 1-2, and FIGS. 4 and 5). Six distinct methyl singlets ($\delta_H$ 1.38, 1.31, 1.27, 0.98, 0.95, 0.89, and 0.80) and an olefinic methine signal ($\delta_H$ 5.38) were observed in the $^1$H NMR spectrum, along with three resonances ($\delta_C$ 180.1, 144.7, and 123.7) in the $^{13}$C NMR spectrum, which were indicative of an oleanane-type triterpenoid (FIG. 4). Furthermore, two oxymethine signals ($\delta_H$ 4.49 and 4.33) and one oxymethylene signal ($\delta_H$ 3.63 and 3.24) were observed, and HSQC, COSY, and HMBC correlations indicated that two oxymethine groups were located at C-2 and C-16, while an oxymethylene group was located at C-23 (FIGS. 6 to 9). Consequently, the aglycone was determined to be polygalacic acid. The relative configuration of the aglycone was deduced by ROESY correlation and comparison with NMR data previously reported (FIGS. 6 and 10).

Figure 11:
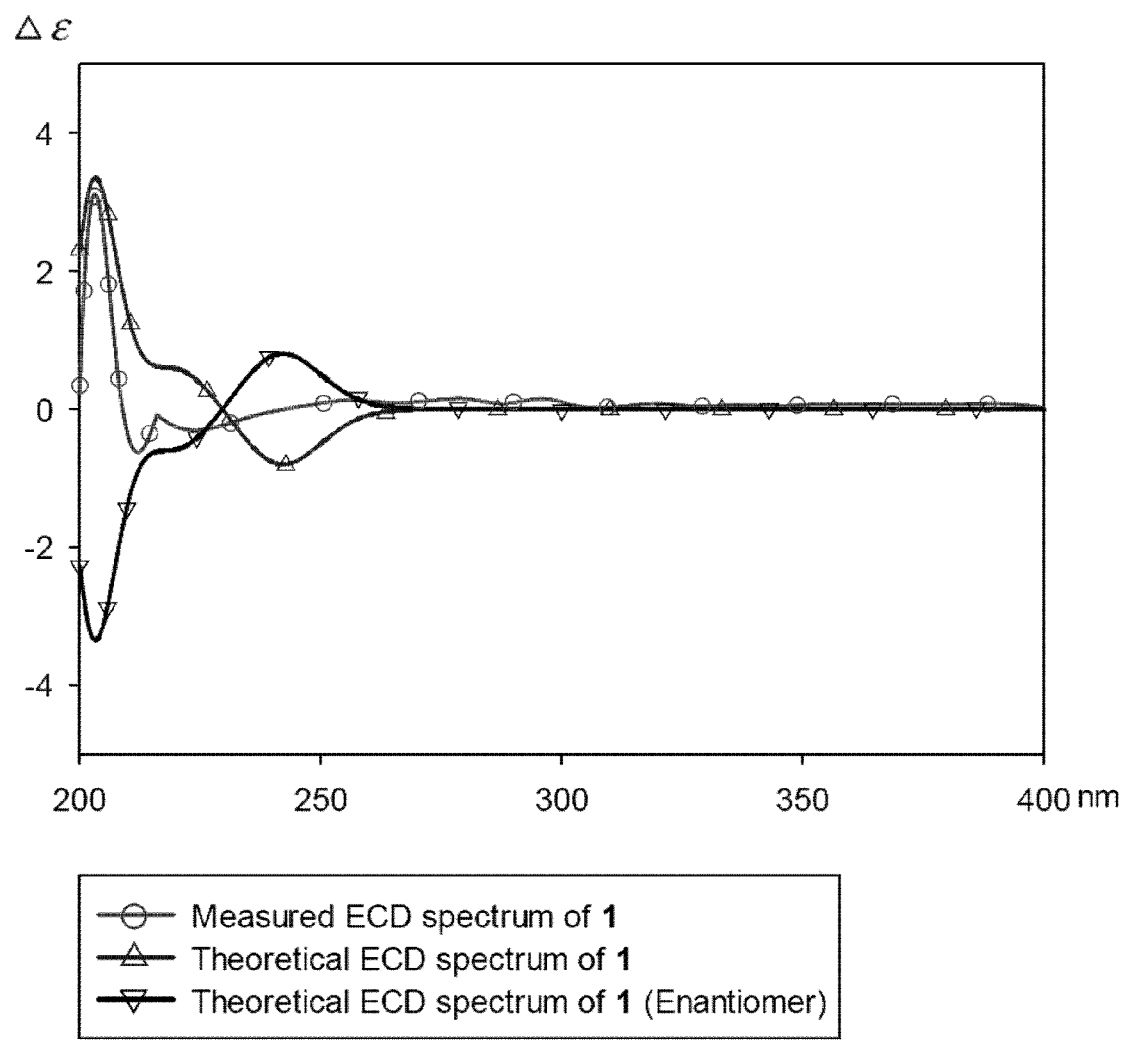
FIG. 11 shows a measured ECD spectrum and a theoretical ECD spectrum of Compound 1 according to an embodiment of the present invention.
Figure 12:
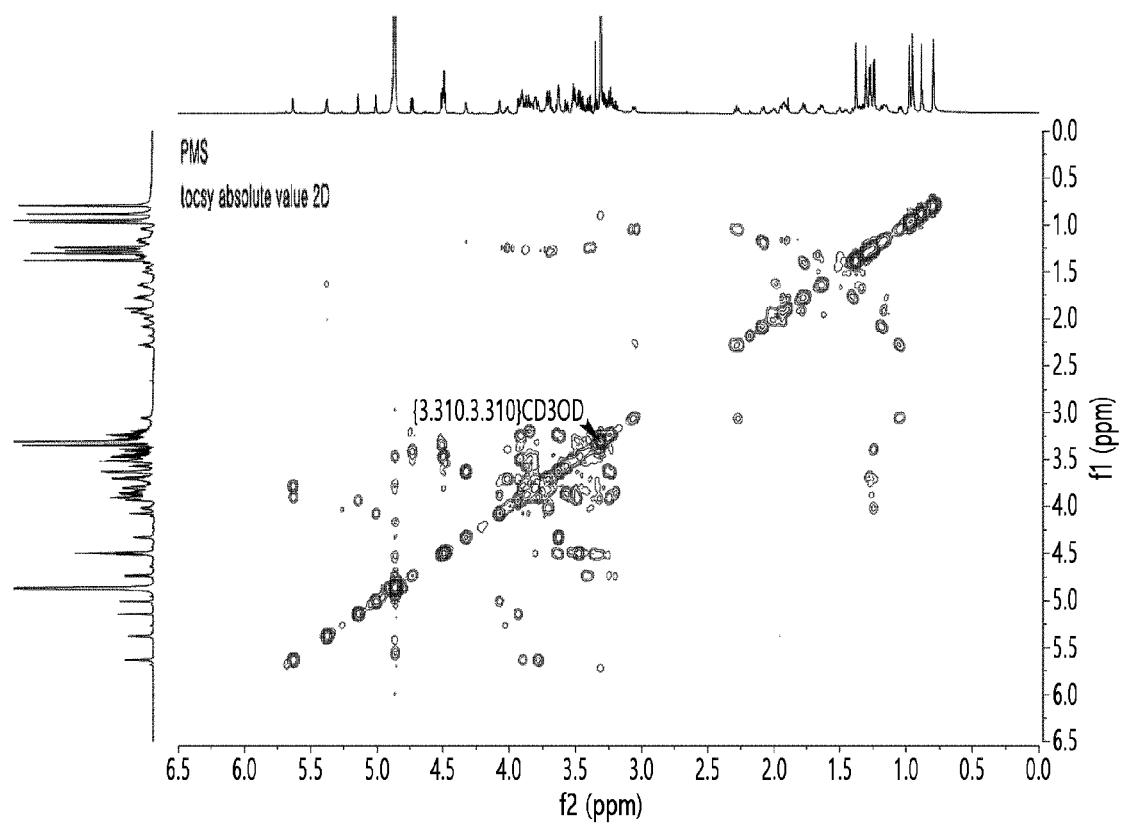
FIG. 12 is a 2D TOCSY spectrum of Compound 1 according to an embodiment of the present invention (600 MHz, $CD_3OD$).
Figure 13:
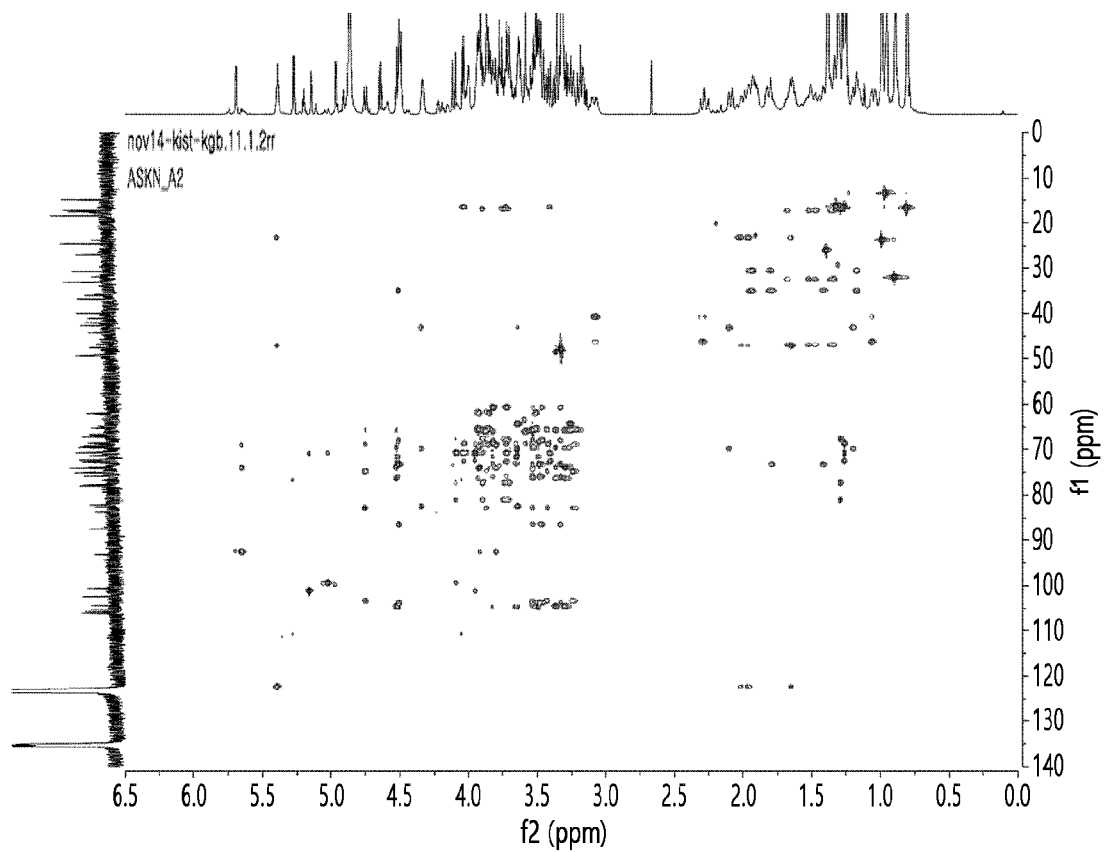
FIG. 13 is a TOCSY-HSQC spectrum of Compound 1 according to an embodiment of the present invention (850 MHz, $CD_3OD$).
Figure 14:
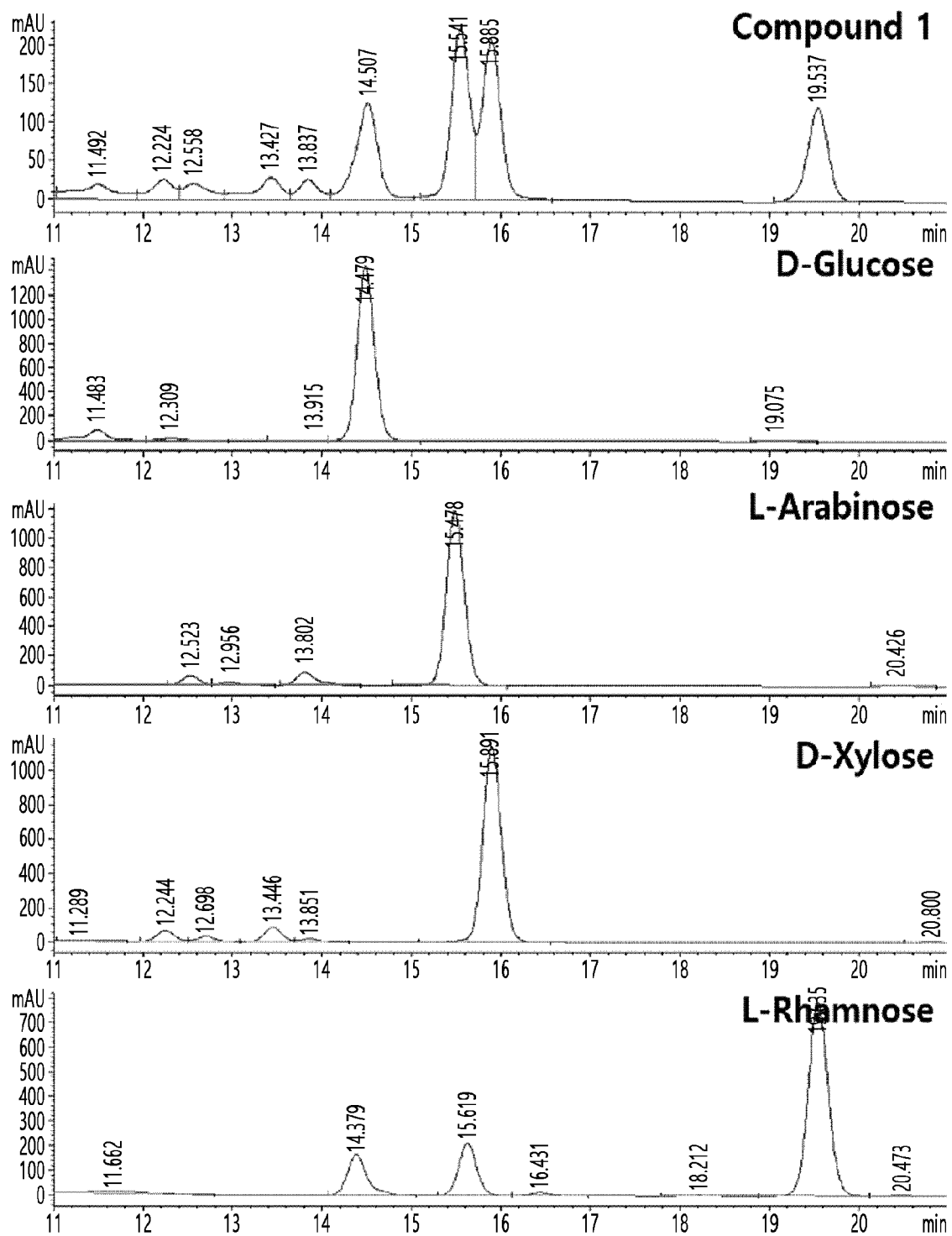
FIG. 14 shows sugar determination of Compound 1 according to an embodiment of the present invention.
Figure 15:
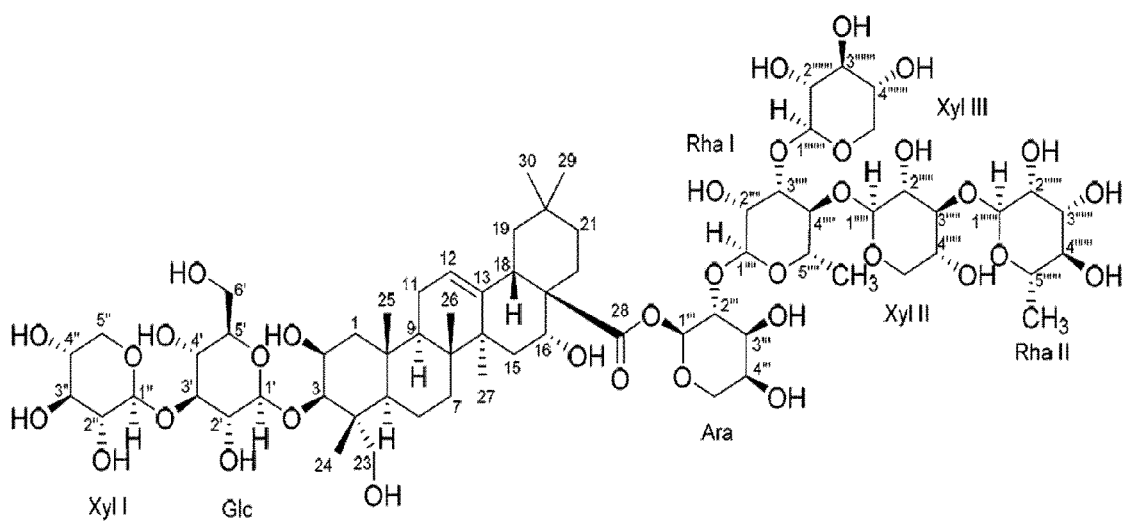
FIG. 15 shows a chemical structure of Compound 1 according to an embodiment of the present invention.

The absolute configuration was determined by using ECD calculation. The measured CD spectrum of Compound 1 exhibited a positive cotton effect (CE) at 203 nm ($\Delta\epsilon$=+3.1). This cotton effect is similar to that ($\Delta\epsilon$=+1.84 at 209 nm) of 2β,3β,16β,23-tetrahydroxy-olean-12-en-28-oic acid methyl ester (methyl polygalacate). The measured circular dichroism (CD) spectrum of Compound 1 was fit well with that of the theoretical ECD spectrum (FIG. 11). In addition, seven characteristic peaks for anomeric protons were observed in a range between 4.40 ppm and 5.70 ppm [$\delta_H$ 5.63 (br d, J=3.0 Hz), 5.14 (br d, J=1.5 Hz), 5.00 (br d, J=1.5 Hz), 4.74 (br d, J=8.0 Hz), 4.51 (br d, J=7.5 Hz), 4.50 (br d, J=7.5 Hz), and 4.49 (br d, J=7.5 Hz)], which were correlated with seven anomeric carbons ($\delta_C$ 93.8, 102.8, 101.3, 105.1, 106.2, 106.3, and 105.3). These coupling constants and chemical shifts suggest that seven sugar moieties were one α-arabinose (Ara), two α-rhamnose (Rha I and Rha II), three β-xylose (Xyl I, Xyl II, and Xyl III), and one β-glucose (Glc). The TOCSY and HSQC-TOCSY correlations enabled the grouping and overall assignment of the $^1$H and $^{13}$C NMR signals of each sugar moiety (FIGS. 12 and 13). The approximate sequence of linkage of sugar moieties was deduced by HR-MS/MS data (FIG. 3). The downfield shifts in the $^1$H NMR spectrum and HMBC correlations from anomeric protons to relevant carbons confirmed the exact position and sequence of sugar moieties (FIG. 6A). According to a previous report, the structure of Compound 1 was similar to that of conyzasaponin K, except the replacement of β-apiose with β-xylose. Acid hydrolysis and comparative studies with standard samples using HPLC demonstrate that these sugar units were L-arabinose, L-rhamnose, D-xylose, and D-glucose (FIG. 14). Consequently, the structure was determined to be 3-O-β-D-xylopyranosyl-(1→3)-β-D-glucopyranosylpolygalacic acid 28-O-α-L-rhamnopyranosyl-(1→3)-β-D-xylopyranosyl-(1→4)-[β-D-xylopyranosyl-(1→3)]-α-L-rhamnopyranosyl-(1→2)-α-L-arabinopyranosyl ester, which is called astersaponin I (FIG. 15).

Example 3: ECD Computation

All computational methods including conformational distribution, optimization, and energy calculation were performed according to methods well known in the art (*J. Nat. Prod.*, 2016, 79(6):1689-1693). Specifically, conformational searches were performed by employing the procedure implemented in the Spartan'14 software under the MMFF molecular mechanics force field, and the conformers were selected for geometry optimizations. Geometry optimizations were operated with DFT calculations at the B3LYP/6-31+G (d,p) level using the Gaussian 09 package. TDDFT ECD calculations for the optimized conformers were performed at the CAM-B3LYP/SVP level with a CPCM solvent model in MeCN. The calculated ECD spectra were simulated with a half bandwidth of 0.3 eV, and the ECD curves were generated using the SpecDis 1.64 software. The ECD spectra were weighted by Boltzmann distribution after UV correction.

Example 4: Autophagy Induction Assay

To investigate the autophagy inducing effect of *A. koraiensis*, human neuroblastoma (SH-SY5Y) cells were cultivated in 6-well plates at a density of 8×10$^5$ cells/well in 2 mL DMEM medium (Gibco) at 37° C. in a humidified atmosphere with 5% $CO_2$. After incubation for 24 hours, the cells were treated with an ethanol extract of *Aster koraiensis* (12.5 μg/mL, 25 μg/mL, and 50 μg/mL), an n-BuOH fraction thereof (12.5 µg/mL, 25 µg/mL, and 50 µg/mL), and Compound 1 isolated from the fraction (5 µM, 10 µM, and 20 µM) prepared according to Example 1, respectively. After additional incubation for 24 hours, the cells were harvested and lysed using a RIPA lysis buffer (Cell Signaling). The protein expression of LC3-II in cell lysates was measured using western blot analysis. A rabbit anti-LC3B primary antibody and a goat anti-rabbit horseradish peroxidase-conjugated IgG secondary antibody (both from Cell Signaling) were used to detect LC3 expression. The immune blots were visualized using an ECL detection kit and analyzed using a LAS-4000 mini system (Fujifilm).

Figure 16:
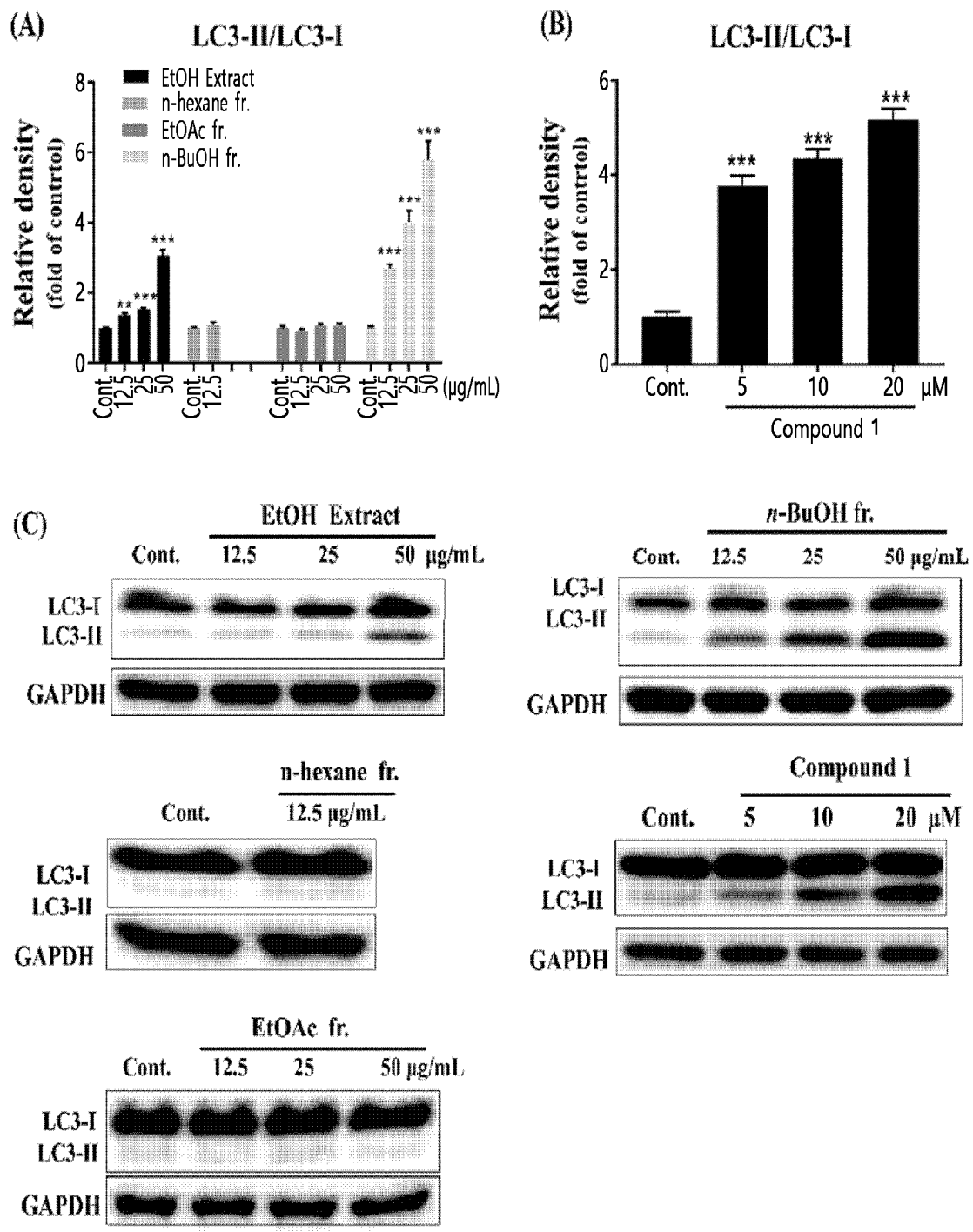
FIG. 16 shows (A) increased LC3-II expression in a dose-dependent manner upon treatment of an ethanol extract of *Aster koraiensis* (12.5 μg/mL, 25 μg/mL, and 50 μg/mL), and an n-hexane fraction (12.5 μg/mL), an ethyl acetate fraction (12.5 μg/mL, 25 μg/mL, and 50 μg/mL), and an n-butanol fraction (12.5 μg/mL, 25 μg/mL, and 50 μg/mL) thereof; (B) up-regulated LC3-II expression in a dose-dependent manner by treatment with astersaponin I; and (C) representative western blot bands of protein marker LC3 in SH-SY5Y cells treated with the ethanol extract of *Aster koraiensis*, fractions thereof (n-hexane, ethyl acetate, and n-butanol), and Compound 1. Data are expressed as mean±SEM (n=3). $p<0.01$, *$p<0.001$ significant difference from control.

The extract, fractions, and astersaponin I (Compound 1) were assessed for effects thereof on autophagy by analyzing the LC3-II/LC3-I ratio in SH-SY5Y cells. The LC3-II/LC3-I ratio has extensively been used as an indicator of autophagy activation because conversion from LC3-I to LC3-II is a necessary process for autophagosome formation. As shown in FIG. 16, treatment with the ethanol extract and n-BuOH fraction significantly increased the ratio of LC3-II/LC3-I in a dose-dependent manner, while n-hexane and ethyl acetate fractions did not show an effect on LC3 expression (FIG. 16A). Interestingly, treatment of Compound 1 led to an increase in the LC3-II/LC3-I ratio in a dose-dependent manner (FIG. 16B), indicating the extent of autophagosome formation and autophagy activation. Previous studies have shown that several triterpene saponins, including ginsenosides, may enhance autophagy in a few cell lines, which are mainly related to cancer. However, autophagy may also have an important role in modulating various neurodegenerative diseases like Parkinson's disease (PD). Therefore, further mechanistic studies will be needed to clarify whether Compound 1 exerts a protective effect on PD through autophagy induction.

Astersaponins are known to exert antitumor, expectorant, and antitussive activities, while no autophagy-inducing effects of astersaponins or conyzasaponins in tumor cells or neuronal cells have been reported. Furthermore, there is no previous literature on astersaponins isolated from *Aster koraiensis*. Astersaponins have been mainly reported from *Aster tataricus* (*J. Nat. Prod.*, 2016, 79:1689-1693). Astersaponin I is the first reported saponin from *A. koraiensis*. The autophagy-inducing constituent of this plant was also reported for the first time in the present invention.

Example 5: Effect of AKNS Sample on mTOR-Dependent Autophagy Signaling Pathway

Figure 17:
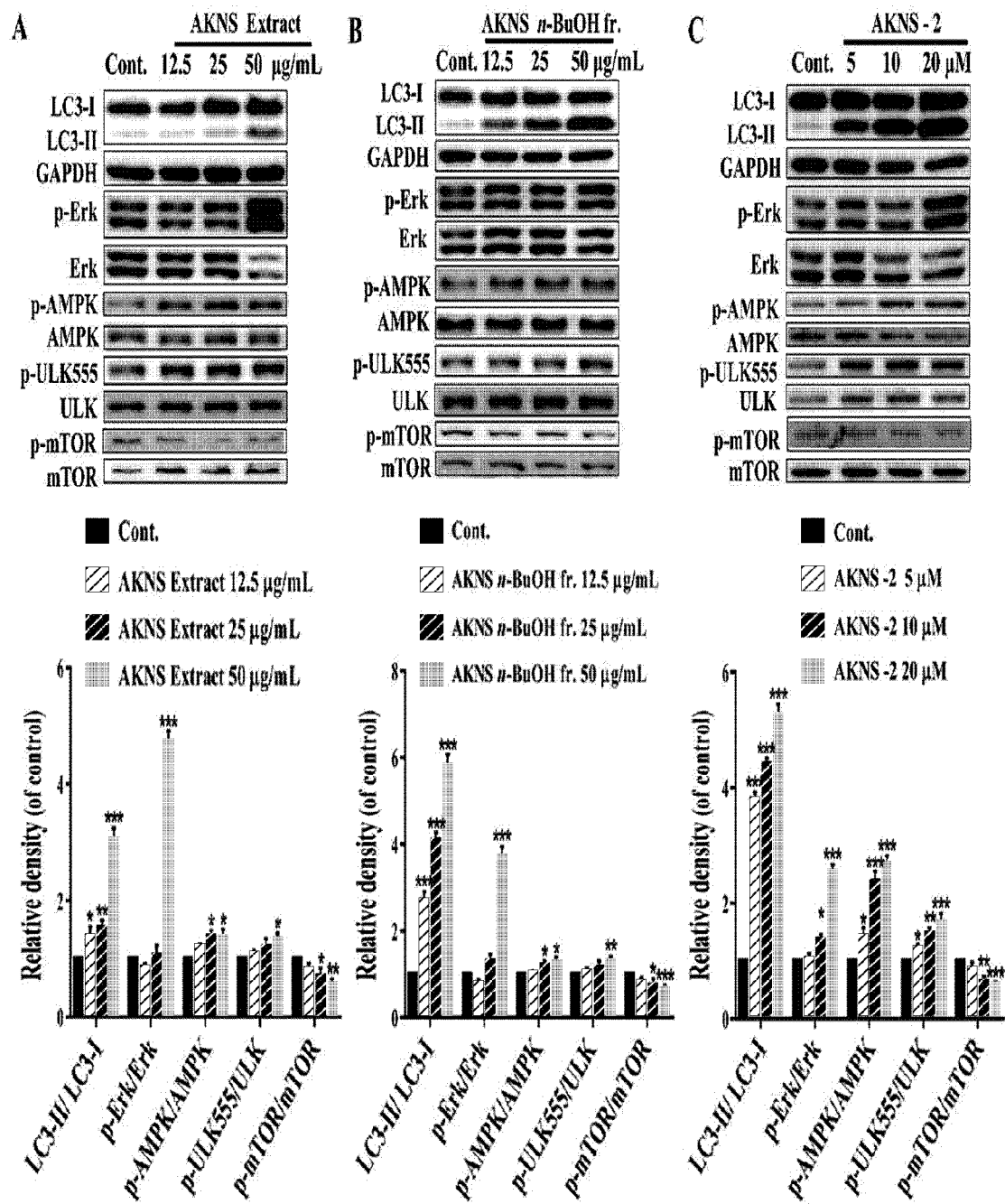
FIG. 17 shows effects of AKNS on mTOR-dependent autophagy signal. After 24 hours from AKNS treatment, primary markers related to autophagy induction were measured in SH-SY5Y cells by western blotting. (A), (B), and (C) show expression of autophagy-related protein markers in SH-SY5Y cells treated with AKNS extract, AKNS n-BuOH fraction, and a single compound AKNS-2, respectively. Data are expressed as mean±SEM (n=3). *p<0.05, p<0.01, *p<0.001 significant difference from control.

In order to investigate autophagy-inducing effects of AKNS samples, SH-SY5Y cells were treated with various concentrations of the AKNS samples (AKNS extract: 12.5 µg/mL, 25 µg/mL, or 50 µg/mL, AKNS n-BuOH fraction: 12.5 µg/mL, 25 µg/mL, or 50 µg/mL, AKNS-2: 5 µM, 10 µM, or 20 µM; and a chemical structure of AKNS-2 is disclosed in FIG. 15). After 24 hours of treatment, expression levels of autophagy-involved protein markers were measured by western blot analysis. As shown in FIG. 17A, the AKNS extract significantly increased the expression level of LC3-II at concentrations of 12.5 µg/mL, 25 µg/mL, and 50 µg/mL. Upon comparison with the conditions of the control, when the cells were treated with the AKNS extract at concentrations of 25 µg/mL and 50 µg/mL, the expression level of p-AMPK significantly increased, and the expression level of p-mTOR significantly decreased. Additionally, significant increases in p-Erk and p-ULK were confirmed in the AKNS extract-treated group at a high dose of 50 µg/mL.

Similarly, as shown in FIG. 17B, upon comparison with the conditions of the control, the AKNS n-BuOH fraction significantly increased the expression level of LC3-II in a dose-dependent manner at a concentration of 12.5 µg/mL, 25 g/mL, or 50 µg/mL. Significant increases in p-Erk and p-ULK were confirmed at a high dose of 50 µg/mL. Also, upon comparison with the conditions of the control, while the expression level of p-AMPK significantly increased, the expression level of p-mTOR significantly increased by AKNS n-BuOH fraction at the concentrations of 25 µg/mL and 50 µg/mL.

Subsequently, autophagy-inducing effects of a single compound (AKNS-2) were identified. As shown in FIG. 17C, AKNS-2 treatment induced the expression of LC3-II, which is an important autophagy marker, in a dose-dependent manner in the SH-SY5Y cells. In addition, while the expression level of p-Erk significantly increased due to AKNS-2 treatment at concentrations of 10 µM and 20 µM, the expression levels of p-AMPK and p-ULK significantly increased by AKNS-2 treatment at concentrations of 5 µM, 10 µM, and 20 µM. The expression of p-mTOR was inhibited by AKNS-2 at concentrations of 10 µM and 20 µM. These results indicate that the AKNS samples activated the AMPK/mTOR pathway and/or the Erk/mTOR pathway, resulting in up-regulation of autophagy.

Figure 18:
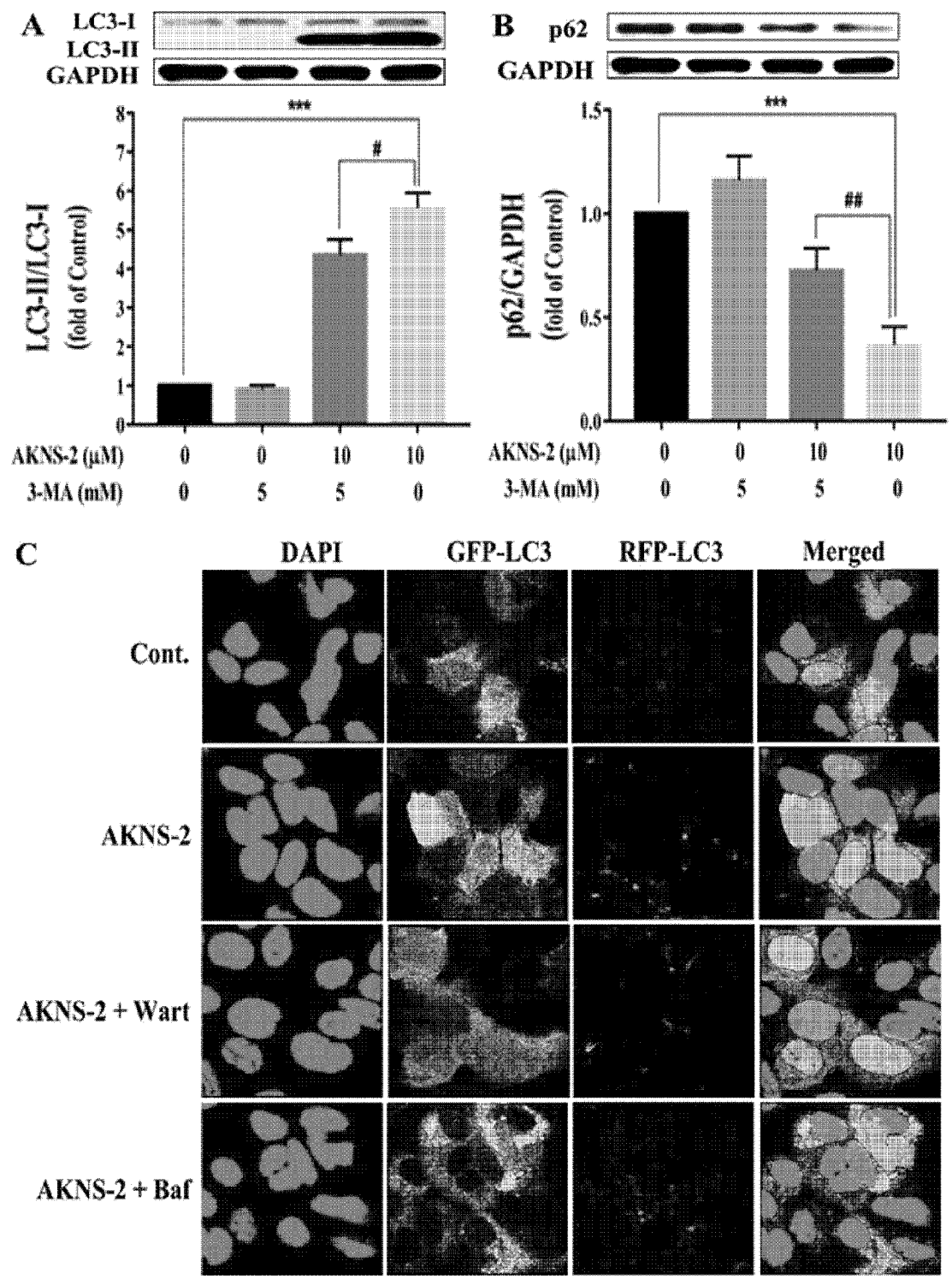
FIG. 18 shows inhibitory effects of autophagy inhibitors on autophagy induced by AKNS-2 in SH-SY5Y cells. (A) indicates that 3-MA (5 mM) decreases LC3-II expression which has been up-regulated by AKNS-2, and (B) indicates that 3-MA increases p62 expression which has been decreased by AKNS-2. (C) shows results of a tandem fluorescent protein quenching assay indicating that AKNS-2-induced autophagy is inhibited by wortmannin (Wart, 50 nM) and bafilomycin $A_1$ (Baf, 100 nM). Data are expressed as mean±SEM (n=3). ***p<0.001 significant difference from control, #p<0.05, ##p<0.01 significant difference from AKNS-2-treated group.

Example 6: Inhibitory Effect of Autophagy Inhibitor on AKNS-2-Activated Autophagy in SH-SY5Y Cells 3-Methyladenine (3-MA) inhibits formation of autophagosomes. In order to identify autophagy activation induced by AKNS-2, accumulation of autophagosomes was inhibited using 3-MA (5 mM) for 30 minutes before treating the SH-SY5Y cells with AKNS-2 (10 µM). As a result, although AKNS-2 (10 µM) significantly increased the expression level of LC3-II (FIG. 18A), the increased expression was significantly decreased by 3-MA; and p62, which also has an important role in autophagy, binds to LC3 via a region called the LC3-interacting region (LIR) and may be degraded when autophagy is activated. Interestingly, AKNS-2 also induced a significant decrease in expression of p62 (FIG. 18B), and 3-MA treatment remarkably blocked the inhibitory effects of AKNS-2 on the expression level of p62. In a tandem fluorescent protein quenching assay, accumulation of GFP-RFP-LC3-II puncta (FIG. 18C) was evaluated using an autophagy sensor of Thermo Fisher Scientific (MA, USA). In the transfected cells treated with AKNS-2 alone, more cytoplasmic puncta stained with green and red fluorescence were observed compared to in the control cells. In order to identify whether AKNS-2 enhances autophagy, the transfected cells were treated with AKNS-2 and wortmannin (Wart; 50 nM) or bafilomycin A, (Baf; 100 nM). While the AKNS-2-enhanced accumulation of green and red LC3-II puncta decreased due to Wart, Baf increased green fluorescence and decreased red fluorescence. This indicates that AKNS-2 activates autophagy.

Figure 19:
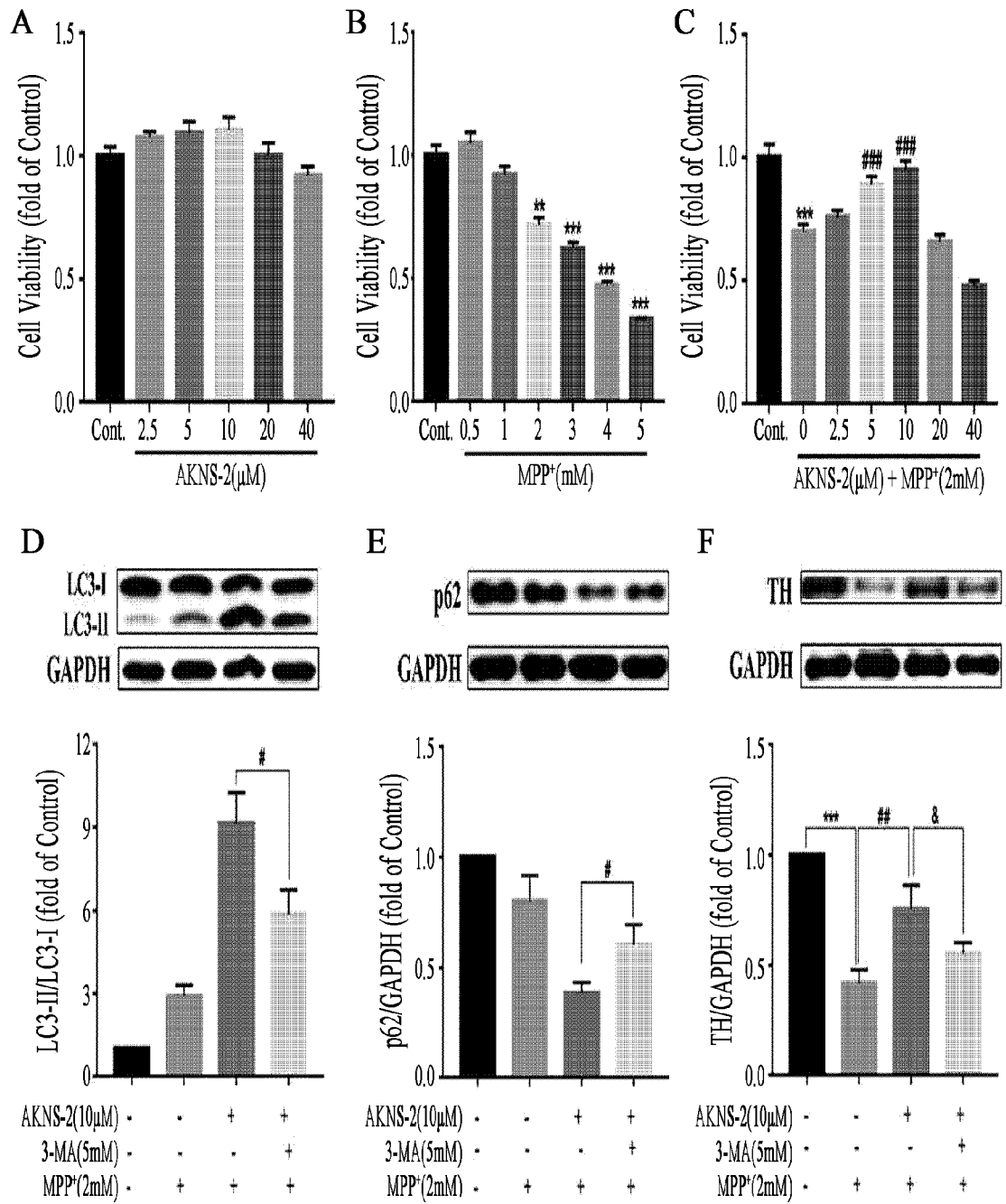
FIG. 19 shows inhibitory effects of autophagy inhibitor 3-MA on protective effects of AKNS-2 against $MPP^+$-induced toxicity in SH-SY5Y cells. (A), (B), and (C) show cell viability of SH-SY5Y cells treated with AKNS-2 alone, $MPP^+$ alone, and both AKNS-2 and $MPP^+$ with various concentrations, respectively. (D), (E), and (F) show expression of LC3, p62, and TH in SH-SY5Y cells treated with AKNS-2 and $MPP^+$ in the presence or absence of 3-MA. Data are expressed as mean±SEM (n=5 for MTT assay and n=3 for western blot analysis). p<0.01, *p<0.001 significant difference from control, #p<0.05, ##p<0.01, ###p<0.001 significant difference from $MPP^+$-treated group. &p<0.05 significant difference from group treated with AKNS-2 and $MPP^+$.

Example 7: Protective Effect on SH-SY5Y Cells Against MPP$^+$-Induced Neurotoxicity by AKNS-2-Activated Autophagy Protective effects of AKNS-2 were identified in an MPP$^+$-induced in vitro PD model. FIG. 19A shows that AKNS-2 did not significantly affect cytotoxicity up to a high concentration of 40 µM in an MTT assay. Working concentrations of MPP$^+$ and AKNS-2 were also determined by the MTT assay. FIG. 19B shows that MPP$^+$ with a concentration of 2 mM significantly decreased cell viability when the SH-SY5Y cells were treated with MPP$^+$ having various concentrations. Accordingly, 2 mM MPP$^+$ was used to induce an in vitro PD model. Subsequently, protective effects of AKNS-2 against MPP$^+$-induced neurotoxicity were tested. Briefly, the SH-SH5Y cells were treated with various concentrations of AKNS-2, and 1 hour later, 2 mM MPP$^+$ was added to the cells. At 24 hours after the treatment, cell viability was detected. As a result (FIG. 19C), it was confirmed that AKNS-2 (5 μM and 10 μM) significantly improved cell viability damaged by 2 mM MPP$^+$.

In order to identify whether AKNS-2 has protective effects on MPP$^+$-impaired SH-SY5Y cells by activating autophagy, autophagy activated by AKNS-2 was blocked using the autophagy inhibitor 3-MA. Upon comparison with a group co-administered with AKNS-2 and MPP$^+$, a 3-MA-treated group significantly inhibited the expression of LC3-II (FIG. 19D), but p62 exhibited inhibition induced by MPP$^+$ (FIG. 19E), and AKNS-2 was restored by 3-MA. Accordingly, autophagy activated by AKNS-2 was blocked by 3-MA. Tyrosine hydroxylase (TH) is expressed by the central nervous system. TH converts tyrosine into L-3,4-dihydroxyphenylalanine (L-DOPA) that may proceed to DA. TH is a rate-limiting enzyme of DA synthesis. Interestingly, in addition to inhibiting autophagy, the MPP$^+$-induced decrease in expression of TH was reversed by AKNS-2 treatment (FIG. 19F), and advantageous effects of AKNS-2 were canceled out by 3-MA treatment.

Example 8: Up-Regulation of Autophagy and Protective Effect Against MPP$^+$ Cytotoxicity in SH-SY5Y Cells by Activating Erk/mTOR Pathway by AKNS-2

Figure 20:
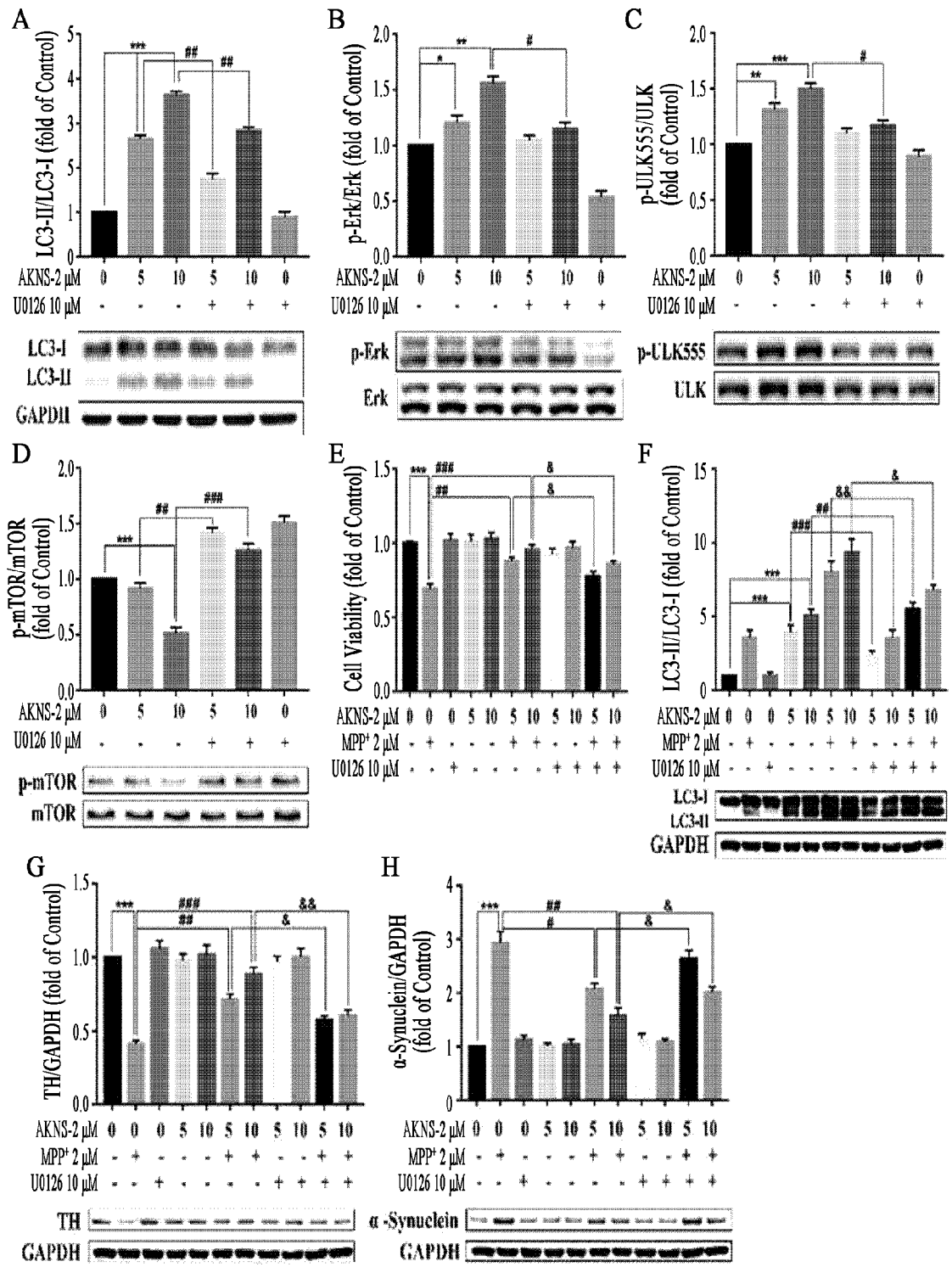
FIG. 20 shows protective effects of AKNS-2 against $MPP^+$-induced toxicity in SH-SY5Y cells by activating an Erk signaling pathway. The SH-SY5Y cells were treated with AKNS-2 (5 μM and 10 μM) in the presence or absence of 10 μM U0126. (A), (B), (C), and (D) show protein expression of LC3, Erk, ULK, and mTOR, respectively. Data are expressed as mean±SEM (n=3). *p<0.05, p<0.01, *p<0.001 significant difference from control, #p<0.05, ##p<0.01, ###p<0.001 significant difference from AKNS-2-treated group. The SH-SY5Y cells were treated with AKNS-2 and $MPP^+$ (2 mM) in the presence or absence of 10 μM U0126. (E) indicates that U0126 cancels out protective effects of AKNS-2 on cell viability; and (F), (G), and (H) show expression of LC3, TH, and α-synuclein, respectively. Data are expressed as mean±SEM (n=5 for MTT assay and n=3 for western blot analysis). ***p<0.001 significant difference from control, #p<0.05, ##p<0.01, ###p<0.001 significant difference from $MPP^+$-treated group (for LC3 difference from AKNS-2-treated group). &p<0.05, &&p<0.01 significant difference from group treated with AKNS-2 and $MPP^+$.

It has been reported that deficiency of Erk may partially inhibit autophagy, and that activation of Erk activates binding to TSC and inhibits mTORC1, and thus autophagy is up-regulated (Int. J. Biochem. Cell. Biol. 2004, 36, 2491-2502). U0126 is an inhibitor of MEK1/2 kinases. The U0126 inhibits activation of Erk1/2 and may be used to study the role of ErK in autophagy induction. In order to identify whether AKNS-2 activates autophagy by regulating the Erk/mTOR signal-transmitting pathway, the SH-SY5Y cells were treated with AKNS-2 (5 μM and 10 μM) in the presence or absence of U0126 (10 μM). 24 hours of incubation, the expression of proteins involved in autophagy induction and the Erk-regulated autophagy pathway was evaluated by western blot analysis. The results are shown in FIG. 20. The expression level of LC3-II was significantly increased by AKNS-2 treatment (5 μM and 10 μM) compared to the conditions of the control. When 10 μM U0126 was added 30 minutes before the AKNS-2 treatment, a significant decrease was observed in the expression of LC3-II (FIG. 20A) in the groups treated with AKNS-2 (5 μM and 10 μM), indicating that AKNS-2-induced autophagy was inhibited by U0126. While significantly increased expression levels of p-Erk were observed in AKNS-2-treated groups (5 μM and 10 μM) compared to the control (FIG. 20B), the increased expression of p-ErK in the cells treated with AKNS-2 (10 μM) was canceled out by administration of 10 μM U0126. Subsequently, expression of p-mTOR was measured (FIG. 20D). Upon comparison with the conditions of the control, AKNS-2 (10 μM) significantly inhibited the expression p-mTOR which had been inhibited, and the expression of p-mTOR inhibited by AKNS-2 (5 μM and 10 μM) was considerably restored when the cells were administered with 10 μM U0126 30 minutes before AKNS-2 treatment. While AKNS-2 (5 μM and 10 μM) significantly increased expression of p-ULK555 as shown in FIG. 20C, 10 μM U0126 canceled out the effects of AKNS-2 (10 μM) on an increase in expression of p-ULK. This indicates that AKNS-2 activates the Erk/mTOR pathway, resulting in up-regulation of autophagy in the SH-SY5Y cells.

TH is a rate-limiting enzyme of DA synthesis. α-Synuclein is a primary constituent of LB, one of the pathologic features of PD. The present invention is intended to study protective effects of AKNS-2 against MPP$^+$-induced neurotoxicity in the SH-SY5Y cells. Cell viability was identified by MTT assay. The results of FIG. 20E indicate that AKNS-2 (5 μM and 10 μM) significantly enhanced cell viability that had decreased by MPP$^+$, but such enhancement was canceled out by treatment with U0126. Next, expression of LC3 was identified (FIG. 20F). These results indicate that U0126 blocked the effects of AKNS-2 (5 μM and 10 μM) on increasing the expression of LC3-II. Similarly, the effects of co-administration of AKNS-2 and MPP$^+$ on increasing the expression of LC3-II were canceled out by administration of U0126. Based on these results, it was confirmed that AKNS-2 improved cell viability, and that AKNS-2 improved autophagy and cell viability by regulating the Erk signal transmission. Also, while expression of TH significantly decreased due to 2 mM MPP$^+$ (FIG. 20G), the decreased expression of TH may be restored by AKNS-2 (5 μM and 10 μM). When U0126 was administered before treatment with AKNS-2 and MPP$^+$, the effects of AKNS-2 on increasing the expression of TH were inhibited. With regard to expression of α-synuclein, 2 mM MPP$^+$ significantly increased the expression of α-synuclein in the SH-SY5Y cells (FIG. 20H), and AKNS-2 treatment canceled out the effects of MPP$^+$ and inhibited the expression of α-synuclein. Interestingly, the protective effects were blocked by the presence of U0126. AKNS-2 reversed the changed expression of TH and α-synuclein and enhanced cell viability that had been reduced by MPP$^+$ treatment in the SH-SY5Y cells. However, such protective effects may be inhibited by disturbing autophagy by blocking the Erk signal-transmitting pathway. This indicates that AKNS-2 activates autophagy by regulating the Erk signal, thereby having protective effects against MPP$^+$-induced cytotoxicity.

Example 9: Up-Regulation of Autophagy and Protective Effect Against MPP$^+$ Cytotoxicity by AKNS-2 Via Activation of AMPK/mTOR Pathway in SH-SY5Y Cells Activation of AMPK induces activation of TSC1/2, and accordingly inhibits the activity of mTOR by activating ULK1, which activates autophagy, and inactivating a TOR activator Rheb. In some cells, knockout of ULK1 blocks autophagy induction, indicating that ULK1 is a factor in the progression of autophagy. In order to identify whether AKNS-2 up-regulates autophagy by regulating the AMPK/mTOR pathway, AMPK signal transmission was disturbed in the SH-SY5Y cells by using AMPK siRNA (50 nM), and then the SH-SY5Y cells were treated with AKNS-2 (5 μM and 10 μM). 24 hours after the AKNS-2 treatment 24, representative protein markers, including LC3, AMPK, mTOR, and ULK, involved in the AMPK/mTOR signal-transmitting pathway and regulating autophagy were measured by western blot analysis. Significantly increased expression of LC3-II (FIG. 21A), p-AMPK (FIG. 21B), and p-ULK555 (FIG. 21C) was observed in the AKNS-2-treated groups compared to the control. Increased expression of LC3-II, p-AMPK, and p-ULK555 by AKNS-2 was significantly decreased in SH-SY5Y cells transfected by AMPK siRNA when compared with SH-SY5Y cells treated with normal AKNS-2. In addition, although AKNS-2 significantly inhibited the expression of p-mTOR (FIG. 21D), the inhibition was canceled out in accordance with the disturbance of AMPK signal transmission.

Figure 21:
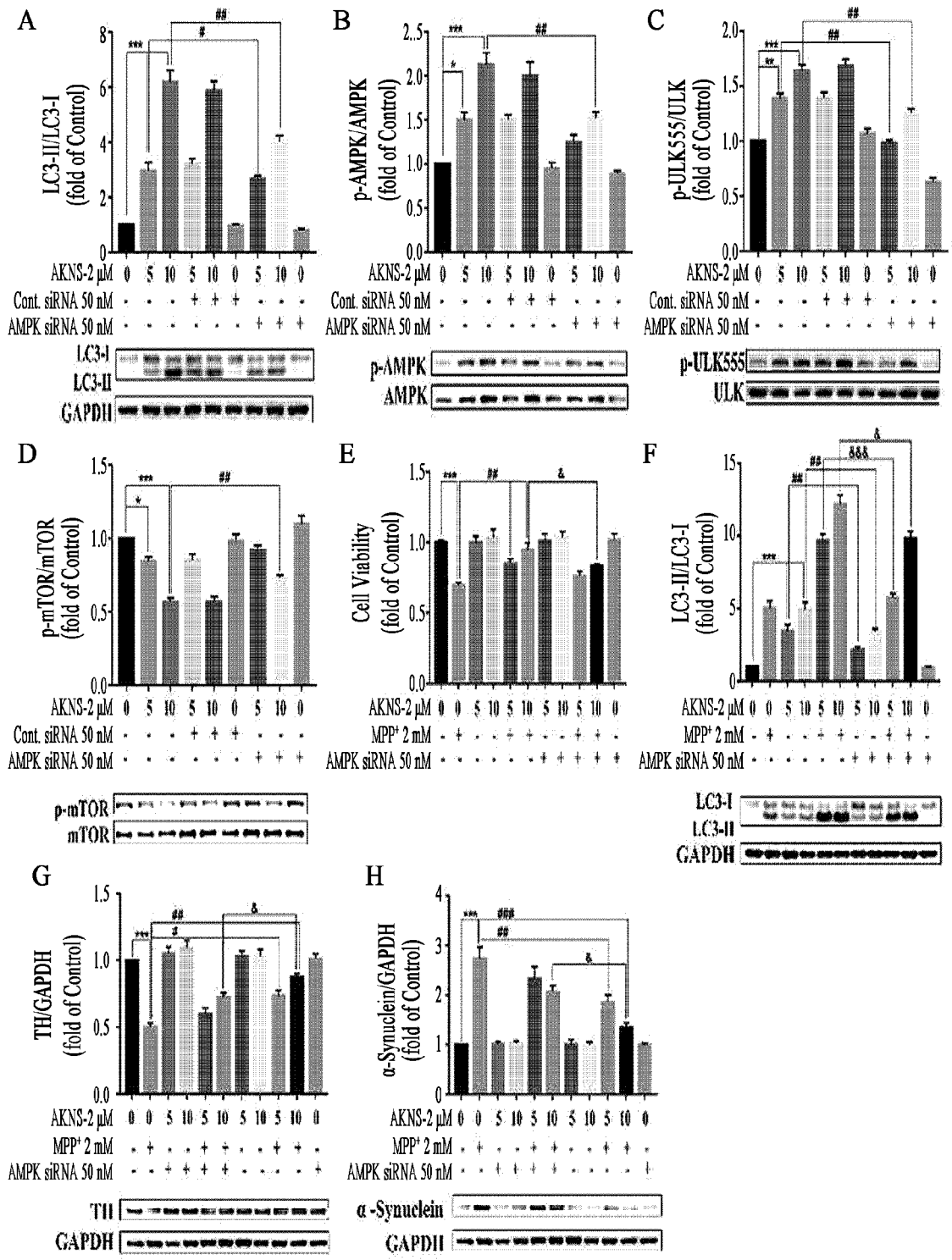
FIG. 21 shows protective effects of AKNS-2 against $MPP^+$-induced toxicity in SH-SY5Y cells by activating an AMPK signaling pathway. (A) to (D) show protein expression of LC3, AMPK, ULK, and mTOR of SH-SY5Y cells treated with AKNS-2 (5 μM and 10 μM) in the presence or absence of AMPK siRNA (50 nM), respectively. Data are expressed as mean±SEM (n=3). *p<0.05, p<0.01, *p<0.001 significant difference from control, #p<0.05, ##p<0.01 significant difference from AKNS-2-treated group. SH-SY5Y cells were treated with AKNS-2 and $MPP^+$ (2 mM) in the presence or absence of AMPK siRNA. (E) indicates that AKNS-2 improves cell viability that has decreased by $MPP^+$ and AMPK siRNA; (F), (G), and (H) show typical absorbance bands and relative densities of LC3, TH, and α-synuclein. Data are expressed as mean±SEM (n=5 for MTT assay and n=3 for western blot analysis). ***p<0.001 significant difference from control, #p<0.05, ##p<0.01, ###p<0.001 significant difference from $MPP^+$-treated group (for LC3 difference from AKNS-2-treated group). &p<0.05 significant difference from group treated with AKNS-2 and $MPP^+$.

Subsequently, it was identified whether AKNS-2 protects the SH-SY5Y cells against $MPP^+$-induced cytotoxicity, and a role of AMPK-mediated autophagy in the protection was identified. The SH-SY5Y cells were transfected with 50 nM AMPK siRNA and then treated with AKNS-2 (5 μM and 10 μM) in the presence or absence of 2 mM $MPP^+$. Cell viability was tested by the MTT assay, and the results are shown in FIG. 21E. As a result, significantly reduced cell viability was observed due to $MPP^+$ treatment when compared with the control, but AKNS-2 (5 μM and 10 μM) reversed the effects of $MPP^+$ on cell viability. Cell viability of the AMPK siRNA-transfected SH-SY5Y cells was far lower than that of normal SH-SY5Y cells in the presence of ANKS-2 and $MPP^+$. With regard to expression of the protein markers, although the expression of LC3-II significantly increased by AKNS-2 (5 μM and 10 μM) in the normal SH-SY5Y cells (FIG. 21F), the expression level of LC3-II of the AMPK siRNA-transfected cells was far lower than that of the normal SH-SY5Y cells in the presence of AKNS-2. Similarly, the expression of LC3-II significantly decreased in the siRNA-transfected cells after co-administration with AKNS-2 and $MPP^+$ compared to the normal cells. Furthermore, the expression of TH significantly decreased by $MPP^+$ treatment (FIG. 21G), and AKNS-2 treatment offset toxicity of $MPP^+$ and reversed the expression of TH. Interestingly, the AKNS-2-mediated increase in the expression of TH was canceled out by AMPK siRNA. $MPP^+$ significantly increased the expression of α-synuclein (FIG. 21H), and the increased expression level of α-synuclein was decreased by AKNS-2 in the normal cells. However, in the AMPK siRNA-transfected cells, inhibitory effects of AKNS-2 on α-synuclein were canceled out. This indicates that AKNS-2 up-regulates autophagy by regulating the AMPK signal transmission, and that activated autophagy protects the SH-SY5Y cells against the $MPP^+$-induced toxicity.

Example 10: Effect of AKNS-2 on Enhancing Behavior Performance of MPTP-Induced In Vivo PD Model The present inventors tested protective effects of AKNS-2 in the $MPP^+$-induced in vitro PD model (schematic diagram in FIG. 22A). First, effects of AKNS-2 on MPTP-impaired behavioral performance were tested by using a rotarod test, a pole test, and a wire hanging test. MPTP was administered to mice for 8 consecutive days after training. At 2 hours, 24 hours, and 48 hours after the last administration of MPTP, behavioral performance was tested in the rotarod test, the pole test, and the wire hanging test. In the rotarod test, although behavioral performance of the mice was significantly impaired at 2 hours and 24 hours when compared with the normal group, the impairment was reversed by administering ropinirole (5 mg/kg) and AKNS-2 (15 mg/kg) at 2 hours and 24 hours. Treatment with AKNS-2 (5 mg/kg) significantly improved MPTP-impaired behavior performance in the rotarod test at 24 hours. At 48 hours, behavior performance of all mice was restored to a normal level (FIG. 22B). MPTP treatment significantly impaired the behavior performance in the pole test at 2 hours after treatment. However, the impaired behavior performance was considerably restored by administering ropinirole and AKNS-2 (5 mg/kg and 15 mg/kg) after 2 hours. At 24 hours and 24 hours after MPTP injection, no significant differences were observed in all groups (FIG. 22C). With regard to the wire hanging test, upon comparison with the conditions of the control, MPTP injection significantly deteriorated latency to fall off at 2 hours and 24 hours. At 48 hours, deterioration of latency induced by MPTP was restored up to a level observed during the pre-training. While ropinirole (5 mg/kg), as a positive control, improved latency deteriorated by MPTP at 2 hours, impaired behavior performance was significantly improved by AKNS-2 (15 mg/kg) at 2 hours and 24 hours in the wire hanging test (FIG. 22D).

Example 11: Protective Effect of AKNS-2 on Mouse Damaged by MPTP Administration

Figure 23:
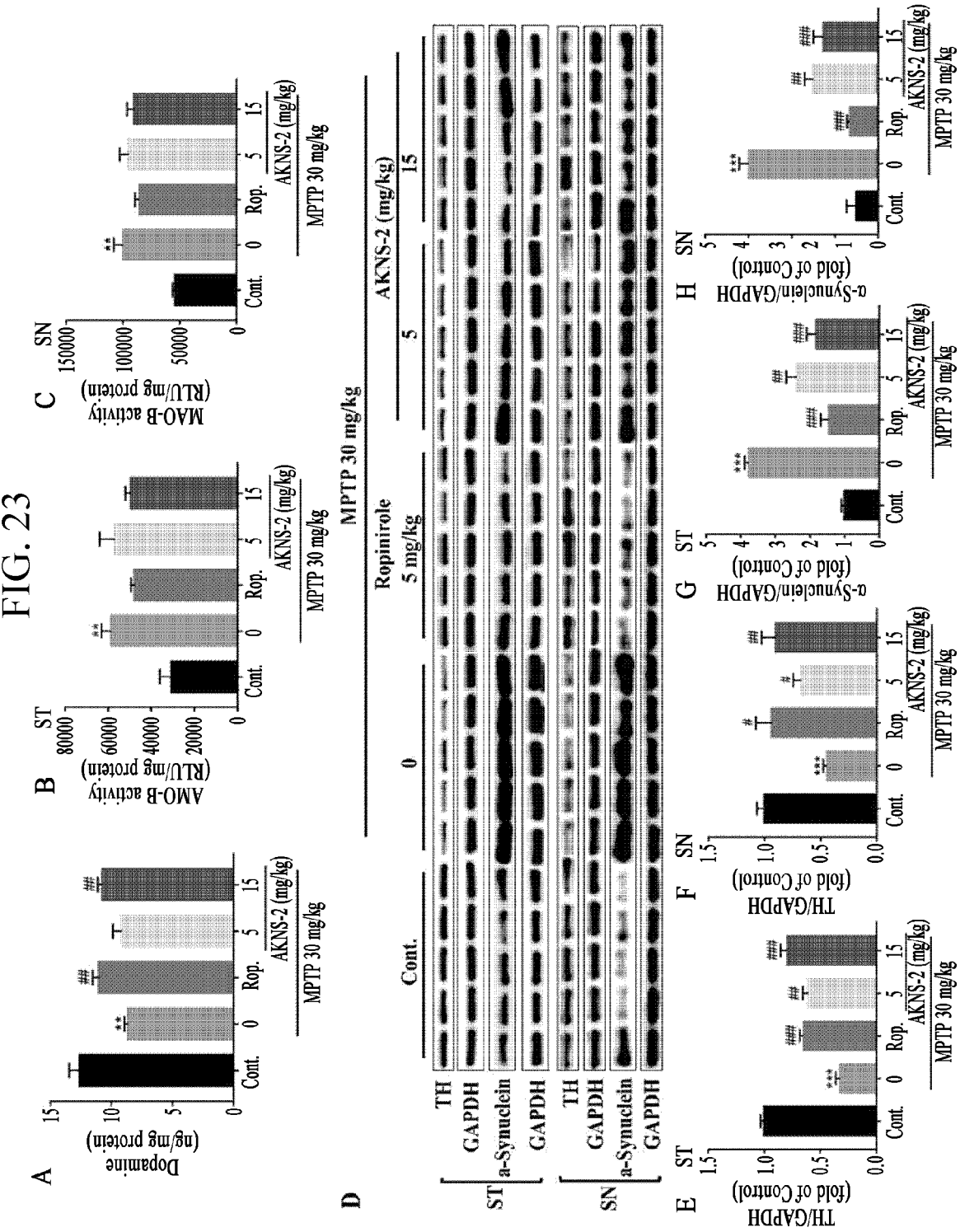
FIG. 23 shows protective effects of AKNS-2 on an $MPP^+$-induced sub-chronic in vitro PD model. After several days from MPTP administration, brain tissue of substantia nigra (SN) and striatum (ST) of mice was excised for biochemical analysis. (A) shows dopamine levels of ST of the groups. (B) and (C) show MAO-B activities of ST and SN. (D) shows typical absorbance bands of TH and α-synuclein in ST and SN. (E) and (F) show relative density of TH of ST and SN, and (G) and (H) show relative density of α-synuclein of ST and SN. Data are expressed as mean±SEM (n=5). p<0.01, *p<0.001 significant difference from control, #p<0.05, ##p<0.01, ###p<0.001 significant difference from MPTP-treated group.
Figure 24A:
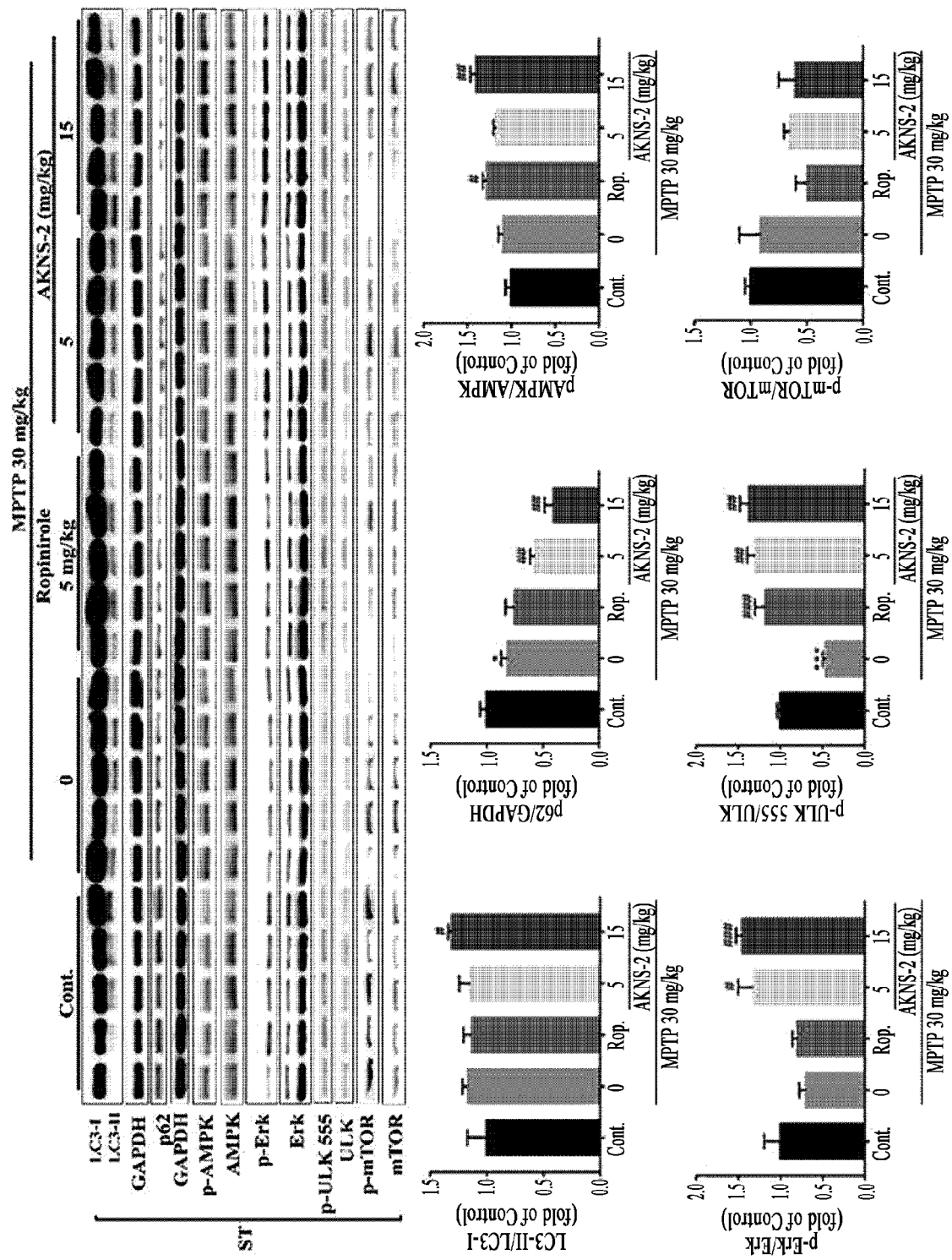
FIGS. 24A and 24B show effects of AKNS-2 on inducing autophagy in an in vivo experiment.
Figure 24B:
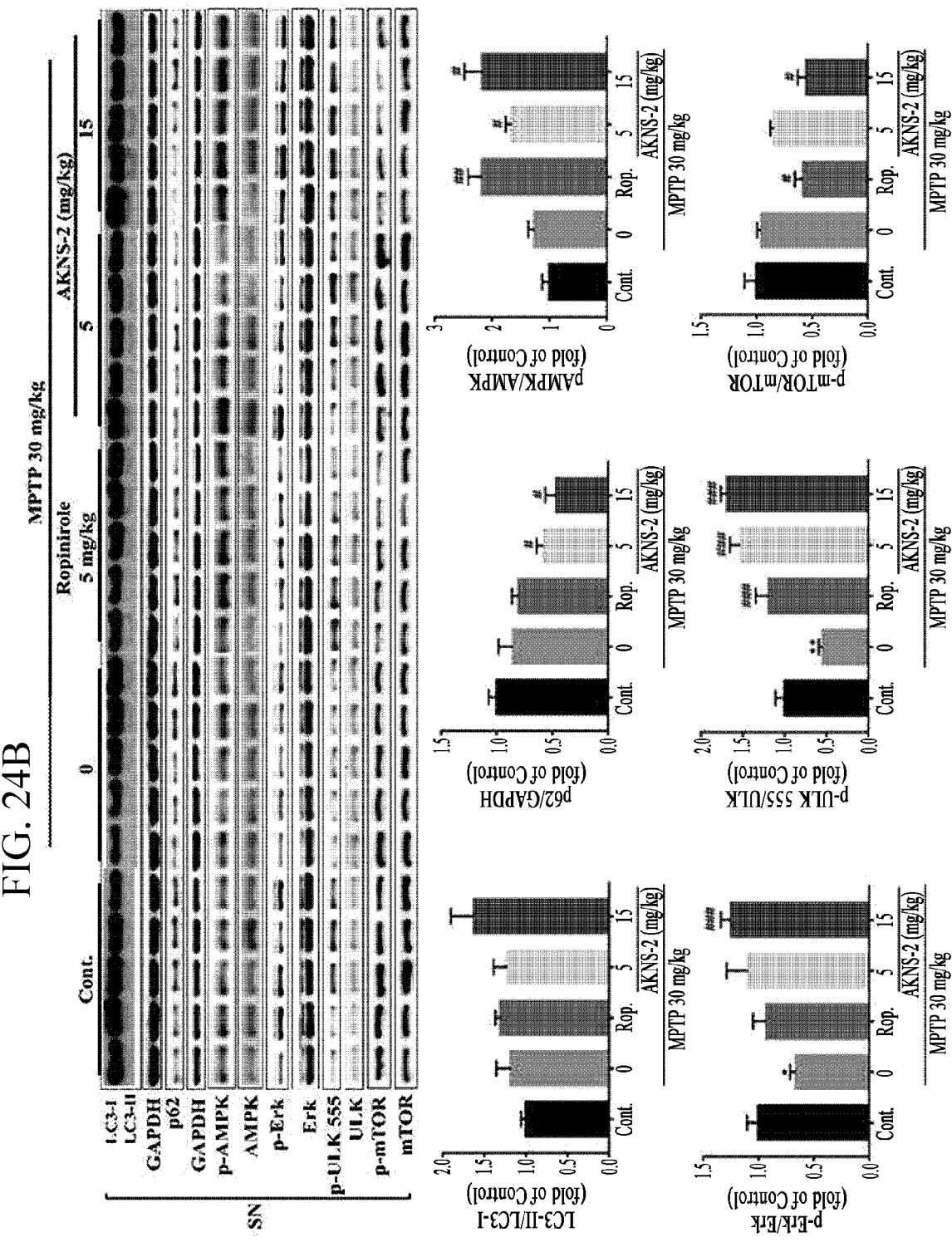

DA is a neurotransmitter that transmits a signal from one neuron to another in the brain. In addition, dopaminergic neuron damage induces loss of DA, causing motor symptoms of PD. The DA level in ST was measured using an ELISA kit (Abnova, Taipei City, Taiwan). As a result, FIG. 23A shows that the DA level significantly decreased by 30 mg/kg MPTP administration in ST. Interestingly, the decrease in the DA level induced by MPTP was restored by ropinirole (5 mg/kg) and AKNS-2 (15 mg/kg). This indicates that AKNS-2 protected dopaminergic neurons against damage induced by MPTP.

MPTP may be converted into $MPP^+$ by MAO-B in glial cells, and $MPP^+$ is an actual toxin that damages dopaminergic neurons. A MAO-B inhibitor inhibits the metabolism of MPTP into $MPP^+$ by blocking the action of MAO-B. The present invention is intended to identify whether dopaminergic neurons may be protected from toxicity of MPTP by inhibiting the activity of MAO-B. In SN and ST, the activity of MAO-B was detected using a MAO-B assay kit (Promega, Woods Hollow Road, Madison, Wis., USA). The results show that MPTP (30 mg/kg) significantly increased the activity of MAO-B in both ST (FIG. 23B) and SN (FIG. 23C). However, AKNS-2 (5 mg/kg and 15 mg/kg) could not reduce the activity of MAO-B that had been increased by MPTP in both ST and SN. This indicates that AKNS-2 is not an efficient MAO-B inhibitor, and that protective effects of AKNS-2 in the MPTP-impaired mice are not caused by inhibition of MAO-B.

The MPTP-induced PD model is characterized by a decrease in TH in dopaminergic neurons. LBs are one of the pathological properties of PD, and α-synuclein is a primary constituent of LBs. In the present invention, expression of TH and α-synuclein were measured in ST and SN of the MPTP-impaired mice by western blot analysis. FIG. 23D shows representative immunoblots of TH and α-synuclein in ST and SN. The TH level significantly decreased in the MPTP-treated group (30 mg/kg) compared to in the normal control in both ST (FIG. 23E) and SN (FIG. 23F). Interestingly, the decreased TH level in both ST and SN was considerably reversed by ropinirole administration (5 mg/kg), as the positive control, and AKNS-2 administration (5 mg/kg and 15 mg/kg). As shown in FIGS. 23G and 23H, the α-synuclein level significantly increased due to MPTP administration in both ST and SN, and a significant decrease in the α-synuclein level was observed in the positive control treated with ropinirole (5 mg/kg) compared to in the MPTP-treated mice. Also, a significant decrease in the α-synuclein level was observed in the AKNS-2-treated mice (5 mg/kg and 15 mg/kg) in both ST and SN compared to in the MPTP-treated mice.

Example 12: Induction of Autophagy by AKNS-2 in MPP⁺-Induced In Vitro PD Model

AKNS-2 induces autophagy in SH-SY5Y cells and protects cells against MPP⁺-induced cytotoxicity due to autophagy activation. The present invention was intended to identify the effects of AKNS-2 on regulating autophagy in the MPP⁺-induced in vitro PD model. At 7 days after treatment with AKNS-2 and MPTP, autophagy-related protein markers were measured in ST and SN using western blot analysis. FIGS. 23A and 23B show representative immunoblots and relative intensities of the protein markers in ST and SN, respectively. This indicates that MPTP increased the expression of LC3-II to some extent, but no noticeable difference was observed in ST and SN. Compared to MPTP treatment, AKNS-2 treatment (15 mg/kg) induced a significant increase in the expression of LC3-II in ST. Although no noticeable difference was observed, increased expression of LC3-II was observed in SN of the AKNS-2-treated group (15 mg/kg). Upon comparison with the normal group, a significant decrease in the expression of p62 was observed in ST of the MPTP-treated group, significantly decreased p62 levels were observed in both ST and SN of the AKNS-2-treated groups (5 mg/kg and 15 mg/kg) compared to the MPTP-treated group. Additionally, MPTP increased the expression level of p-AMPK in both ST and SN. Compared to MPTP treatment, treatment with ropinirole and AKNS-2 induced a significant increase in p-AMPK in both ST and SN. Furthermore, upon comparison with the conditions of the control, expression of p-Erk in both ST and SN decreased due to MPTP treatment (30 mg/kg) and significantly increased due to AKNS-2 treatment (15 mg/kg) compared to MTPT treatment. Similar to p-Erk expression, the p-ULK level noticeably decreased by MPTP administration in ST and SN, and treatment with ropinirole and AKNS-2 (5 mg/kg and 15 mg/kg) canceled out the effects of MPTP and significantly increased the expression of p-ULK in ST and SN. Also, the present inventors measured the expression of p-mTOR in mice, and no significant difference was observed in ST or SN between the normal group and the MPTP-treated group. Although no noticeable decrease was observed, ropinirole and AKNS-2 clearly showed a tendency to decrease the expression of p-mTOR in ST. In SN, a significant decrease in p-mTOR was confirmed in the groups treated with ropinirole and AKNS-2.

The invention claimed is:

1. A pharmaceutical composition for preventing or treating a neurodegenerative disorder comprising a compound represented by Formula 1 or a pharmaceutically acceptable salt thereof as an active ingredient; gelatin as an excipient; and a lubricant, wherein the pharmaceutical composition is a solid formulation for oral administration:

[Formula 1]

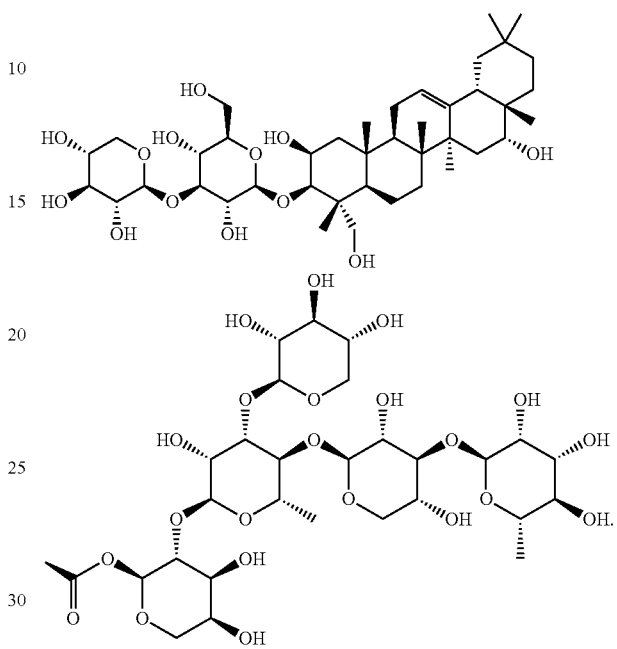

2. The pharmaceutical composition of claim 1, wherein the neurodegenerative disorder is one selected from the group consisting of Parkinson's disease (PD), Alzheimer's disease (AD), amyotrophic lateral sclerosis (ALS), Huntington's disease (HD), fronto-temporal dementia, cortico-basal degeneration, and progressive supranuclear palsy (PSP).

3. The pharmaceutical composition of claim 1, wherein the neurodegenerative disorder is Parkinson's disease.

4. The pharmaceutical composition of claim 1, wherein the prevention or treatment of the neurodegenerative disorder is achieved by inhibition of brain cell death via autophagy-inducing action.

5. The pharmaceutical composition of claim 1, further comprising a pharmaceutically acceptable carrier.

6. The pharmaceutical composition of claim 1, wherein the compound represented by Formula 1 or a pharmaceutically acceptable salt thereof is an alcohol extract of *Aster koraiensis*, wherein the alcohol extract is fractionated using n-butanol.

* * * * *